US007732423B2

(12) United States Patent
Michel et al.

(10) Patent No.: US 7,732,423 B2
(45) Date of Patent: *Jun. 8, 2010

(54) NUCLEOTIDE VECTOR, COMPOSITION CONTAINING SUCH VECTOR, AND VACCINE FOR IMMUNIZATION AGAINST HEPATITIS

(75) Inventors: Marie-Louise Michel, Paris (FR); Maryline Mancini, Paris (FR)

(73) Assignees: Institut Pasteur, Paris (FR); Institut National de la Sante et de la Recherche Medicale, Paris (FR)

(*) Notice: Subject to any disclaimer, the term of this patent is extended or adjusted under 35 U.S.C. 154(b) by 169 days.

This patent is subject to a terminal disclaimer.

(21) Appl. No.: 11/978,673

(22) Filed: Oct. 30, 2007

(65) Prior Publication Data
US 2009/0093428 A1    Apr. 9, 2009

Related U.S. Application Data

(63) Continuation of application No. 10/142,358, filed on May 10, 2002, now abandoned, which is a continuation of application No. 09/570,546, filed on May 12, 2000, now Pat. No. 6,429,201, which is a continuation of application No. 08/799,569, filed on Feb. 12, 1997, now Pat. No. 6,133,244, which is a continuation-in-part of application No. 08/706,337, filed on Aug. 30, 1996, now abandoned, which is a continuation-in-part of application No. 08/633,821, filed as application No. PCT/FR94/00483 on Apr. 27, 1994, now abandoned.

(51) Int. Cl.
C07K 14/02    (2006.01)
C07K 14/005   (2006.01)
A61K 48/00    (2006.01)
C12N 15/63    (2006.01)

(52) U.S. Cl. .................. 514/44 R; 435/320.1
(58) Field of Classification Search ......... 514/44 R; 435/320.1, 235.1
See application file for complete search history.

(56) References Cited

U.S. PATENT DOCUMENTS

| | | | |
|---|---|---|---|
| 4,769,238 A | 9/1988 | Rutter et al. ............ 424/89 |
| 5,256,553 A | 10/1993 | Overall et al. ........ 435/172.2 |
| 5,256,767 A | 10/1993 | Salk et al. ............ 530/350 |
| 5,310,668 A | 5/1994 | Ellis et al. .......... 435/172.3 |
| 5,593,972 A | 1/1997 | Weiner et al. ........... 514/44 |
| 5,639,637 A | 6/1997 | Thomas et al. ......... 435/69.3 |
| 5,643,578 A | 7/1997 | Robinson et al. ...... 424/210.1 |
| 6,133,244 A * | 10/2000 | Michel et al. ........... 514/44 |
| 6,429,201 B1 | 8/2002 | Michel et al. |

FOREIGN PATENT DOCUMENTS

EP    0 998 301 A1    5/2000
WO    8806185        8/1988
WO    9206212        4/1992

OTHER PUBLICATIONS

Mancini et al. DNA-mediated Immunization in a Transgenic Mouse Model of the Hepatitis B Surface Antigen Chronic Carrier State. PNAS, vol. 93, pp. 12496-12501, Oct. 1996.*
Davis et al. DNA-based Immunization Induces Continuous Secretion of Hepatitis B Surface Antigen and High Levels of Circulating Antibody. Human Molecular Genetics, vol. 2, No. 11, pp. 1847-1851, 1993.*
Babinet et al. Specific Expression of Hepatitis B Surface Antigen (HBsAg) in Transgenic Mice. Science, vol. 20, pp. 1160-1163, Dec. 6, 1985.*
Mancini et al. Induction of Anti-Hepatitis B Surface Antigen (HBsAg) Antibodies in HBsAg Producing Transgenic Mice: A Possible Way of Circumventing "Nonresponse" to HBsAg. Journal of Medical Virology, vol. 39, pp. 67-74, 1993.*
Davis, Heather L. DNA Vaccines for Prophylactic or Therapeutic Immunization Against Hepatitis B Virus. The Mount Sinai Journal of Medicine, vol. 66, pp. 84-90, Mar. 1999.*
Chisari et al. A Transgenic Mouse Model of the Chronic Hepatitis B Surface Antigen Carrier State. Science, vol. 230, pp. 1157-1160, Dec. 6, 1985.*
Akbar et al. Placebo-controlled Trial of Vaccination with Hepatits B Virus Surface Antigen in Hepatitis B Virus Transgenic Mice. Journal of Hepatology, vol. 26, pp. 131-137, 1997.*
Araki et al. Expression and Replication of Hepatitis B Virus Genome in Transgenic Mice. PNAS, vol. 86, pp. 207-211, Jan. 1989.*
Akbar et al. Hepatitis B Virus (HBV)-Transgenic Mice as an Investigative Tool to Study Immunopathology During HBV Infection. Int. J. Exp. Path., vol 79, pp. 279-291, 1998.*
Wang et al., PNAS, 90:4156-60 (1993).
Z. Li et al., *Devel.*, 117:947-59 (1993).
M. Lubeck et al., PNAS 86:6763-7 (1989).
P. Valenzuela et al., *Nature*, 298:347-350 (1982).
J. Ulmer et al., *Science*, 251:1745-9 (1993).
C. Shihet et al., *J. Virol.*, 67(10)5823-32 (1993).
R. Cattaneo et al., *Nature*, 305:336-8 (1983).
D. Milich et al., *J. Immunol.*, 137(1):315-22 (1986).
D. Thomson et al., *PNAS*, 81:659-63 (1984).
B. Haynes et al., *Science*, 260:1279-86 (1993).
W. Szmuness et al., *N. Engl. J. Med.*, 307(24):1481-6 (1982).
W. Bohmet et al., *J. Immunol. Med.*, 193:29-40 (1996).

(Continued)

Primary Examiner—Peter Paras, Jr.
Assistant Examiner—David Montanari
(74) Attorney, Agent, or Firm—Finnegan, Henderson, Farabow, Garrett & Dunner, L.L.P.

(57) ABSTRACT

Nucleotide composition containing a vector and vaccine for immunization against hepatitis. Nucleotide vector comprising at least one gene or one complementary DNA coding for at least a portion of a virus, and a promoter providing for the expression of the gene in muscle cells. The gene may be the S gene of the hepatitis B virus. A nucleotide vector composition when administered to even chronic HBV carriers is capable of breaking T cell tolerance to the surface antigens of hepatitis B virus. A vaccine preparation containing bare DNA is injected into the host previously treated with a substance capable of inducing a coagulating necrosis of the muscle fibers.

18 Claims, 16 Drawing Sheets

OTHER PUBLICATIONS

Zinkernagel, Fundamental Immunology, 3$^{rd}$ edition, Raven Press, Paul, W.-editor, Chapter 34, pp. 1211-1250 (1993).
Ledley, *Human Gene Therapy*, 2:77-83 (1991).
Okin et al., Report and Recommendations of the Panel to Assess the NIH Investment in Research on Gene Therapy, Distributed by the National Institutes of Health, Bethesda, MD, or www.nih.gov (Dec. 7, 1995).
Chattergoon et al., *FASEB*, 11:753-763 (1997).
McDonnell et al., *The New England Journal of Medicine*, 334:42-45 (1996).
Mancini et al., *PNAS*, 93:12496-12501 (1996).
Davis et al., *Human Molecular Genetics*, 2(11):1847-1851 (1993).
Babinet et al., *Science*, 20:1160-1163 (1985).
Mancini et al., *Journal of Medical Virology*, 39:67-74 (1993).
Davis, *The Mount Sinai Journal of Medicine*, 66:84-90 (1999).
Chisari, et al. *Science*, 230:1157-1160 (1985).
Akbar et al., *Journal of Hepatology*, 26:131-137 (1997).
Aaraki et al., *PNAS*, 86:207-211 (1989).
Akbar et al., *Int. J. Exp. Path.*, 79:279-291 (1998).
Xu et al., "Molecular therapeutics of HBV," *Current Gene Therapy*, 3:341-355 (2003).
Griffin, "A strategic approach to vaccine development: animal models, monitoring vaccine efficacy, formulation and delivery," *Advanced Drug Delivery Reviews*, 54:851-861 (2002).
Yap et al., "Recombinant DNA hepatitis B vaccine containing Pre-S components of the HBV coat protein—a preliminary study on immunogenicity," *Journal Viral Hepat.*, 1:79-83 (1994).
Babiuk et al., "Induction of immune responses by DNA vaccine in large animals," *Vaccine*, 21:649-658 (2003).
Hilleman, "Vaccines in historic evolution and perspective: a narrative of vaccine discoveries," *Vaccine*, 8:1436-1447 (2000).
Yap, Recombinant DNA hepatitis B vaccine containing Pre-S components of the HBV coat protein—a preliminary study on immunogenicity, *Vacine*, 10(7):439-42 (1992).
Milch, "Immune response to hepatitis B virus proteins: relevances of the murine model," *Semin Liver Dis.*, 11(2), Abstract (1991.

* cited by examiner

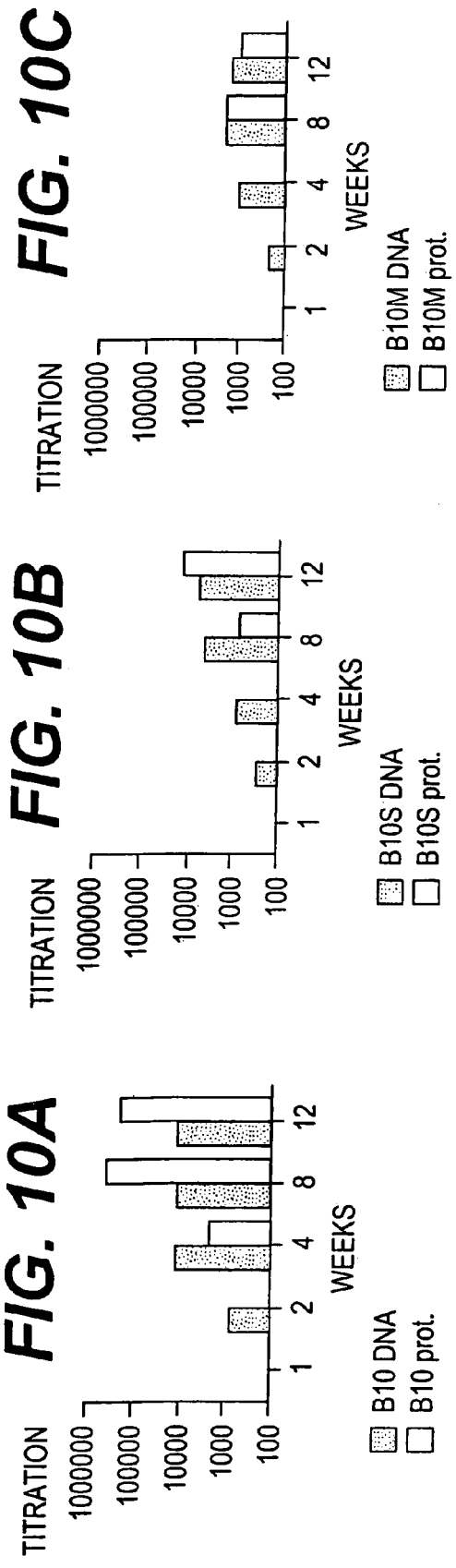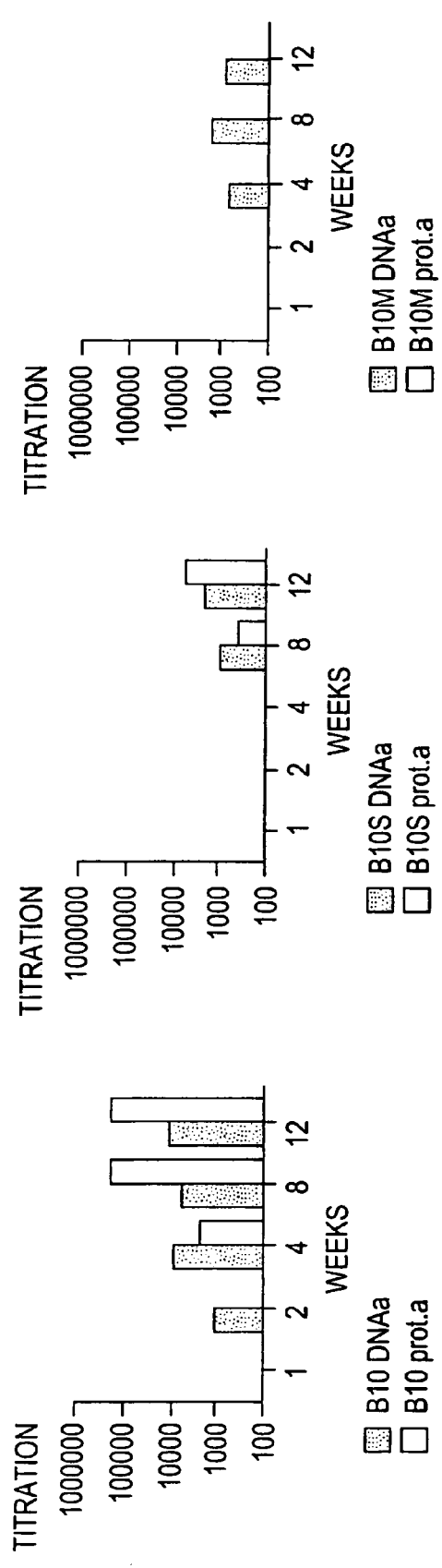

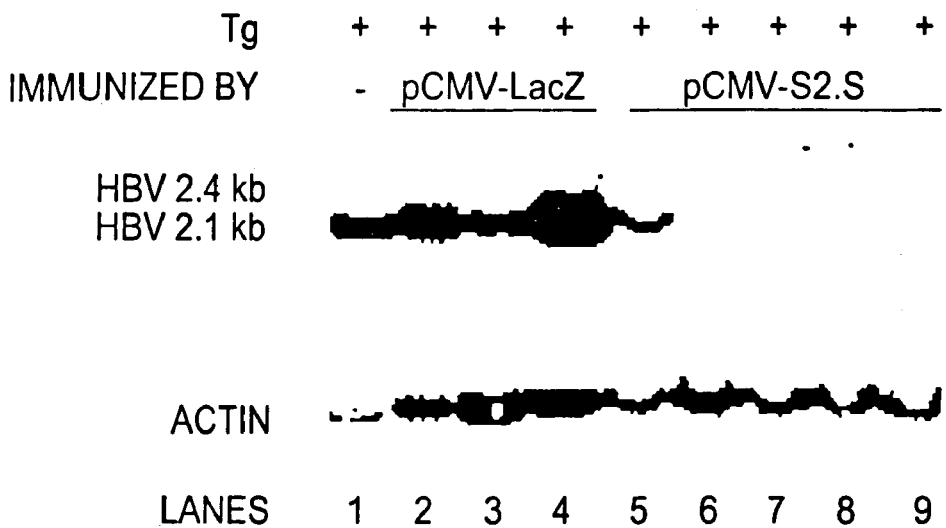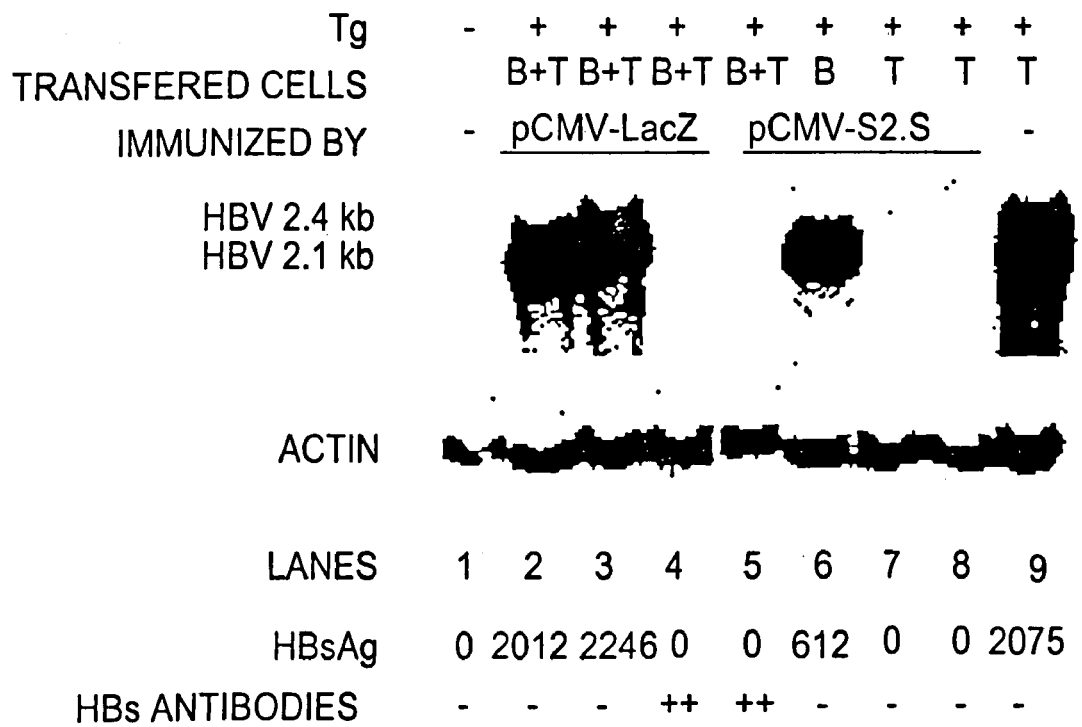
FIG. 15

NUCLEOTIDE VECTOR, COMPOSITION CONTAINING SUCH VECTOR, AND VACCINE FOR IMMUNIZATION AGAINST HEPATITIS

CROSS-REFERENCE TO RELATED APPLICATIONS

This application is a continuation of application Ser. No. 10/142,358, filed May 10, 2002, now abandoned, which is a continuation of application Ser. No. 09/570,546, filed May 12, 2000, now U.S. Pat. No. 6,429,201, which is a continuation of application Ser. No. 08/799,569, filed Feb. 12, 1997, now U.S. Pat. No. 6,133,244, which is a continuation-in-part of application Ser. No. 08/706,337, filed Aug. 30, 1996, now abandoned, which is a continuation-in-part of application Ser. No. 08/633,821, filed Aug. 2, 1996, now abandoned, which is a 371 of PCT/FR94/00483, filed Apr. 27, 1994.

BACKGROUND OF THE INVENTION

The present invention relates to compositions for inducing protective antibodies against hepatitis. It also relates to a vector comprising a nucleotide sequence coding for at least a portion of a virus protein, which is capable of being expressed in muscle cells. In addition, the invention relates to compositions capable of inducing a T cell response in chronic HBV carriers.

Hepatitis B is a widespread and serious international health problem. In addition to causing acute hepatitis and liver damage, the hepatitis B virus (HBV) can cause cirrhosis and hepatocellular carcinoma (Davis, Hum. Molec. Genet. 2:1847-1851 (1993)).

The HBV is a 42-nm particle (Dane particle) consisting of a lipoprotein envelope enclosing a core protein (capsid) and the viral genome, which contains only four genes (S, C, P, X). The major (or small) envelope protein, which includes the surface antigen of HBV (HBsAG) is encoded by the S gene and is organized into dimers of one glycosylated and one unglycosylated polypeptide (Petersen, J. Biol. Chem. 256: 6975-6983 (1981)). Present in smaller amounts are the middle and large envelope proteins, which are encoded by the pre-S2 and S or pre-S1, pre-S2 and S genes, respectively. The predominant form of HBsAg secreted by infected cells is not the Dane particle, however, but 22-nm particles or filaments, which are empty viral envelopes composed solely or predominantly of major (small) envelope protein and sometimes small amounts of middle and large proteins (Maupas, Lancet 1:1367-1370 (1976)). The 22-nm particles are seen to persist in the plasma of chronic carriers (Davis, 1993).

In 1976, the first vaccine against HBV comprising 22-nm HBsAg particles was applied to humans (Maupas, 1976). The particles were purified from the plasma of chronic carriers and treated to eliminate possible co-purified infectious HBV or other pathogens. While this vaccine was effective, mass immunization was not feasible due to the long and expensive purification procedure, the need to assay each batch on chimpanzees for safety, and the limited supply of chronically infected human plasma (Maugh, Science 210:760-762 (1980); Stephenne, Vaccine 6:299-303 (1988)).

The present vaccines are produced employing genetic engineering techniques to create HBsAg-producing cell lines. One frequently used vaccine is a second generation vaccine based on recombinant yeast cells containing the S gene for HBsAg (Valenzuela, Nature 298:347-350 (1982)). Another vaccine commonly used in France is a third generation vaccine based on a line of Chinese hamster ovary cells containing both the S and pre-S2 genes (Michel, Proc. Natl. Acad. Sci. USA 81:7708-7712 (1984)). While the present protein vaccines are highly effective and safe, the production and maintenance of these vaccines is time-consuming and expensive (Davis, 1993). On the other hand, the production of a viral vaccine is not feasible due to safety considerations.

Immunization by DNA-based vaccines has been the object of several studies since the beginning of the 1990s. A DNA-based vaccine involves the transfer of a gene or at least a portion of a gene, by direct or indirect means, such that the protein subsequently produced acts as an antigen and induces a humoral- and/or cellular-mediated immunological response.

Ulmer et al. (Science, 259:1745-1749 (1993)) obtained protection against the influenza virus by induction of the cytotoxic T lymphocytes through injection of a plasmid coding for the influenza A nucleoprotein into the quadriceps of mice. The plasmid used carries either the Rous sarcoma virus promoter or the cytomegalo virus promoter.

Raz et al. (Proc. Natl. Acad. Sci. USA 90:4523-4527, (1993)) injected vectors comprising the Rous sarcoma virus promoter and a gene coding for interleukin-2, interleukin-4, or the β1-type transforming growth factor (TGF-β 1). The humoral and cell-mediated immune responses of the mice to which these plasmids have been intramuscularly administered are improved.

Wang et al. (Proc. Natl. Acad. Sci. USA, 90:4156-4160, (1993)) injected a plasmid carrying a gene coding for the envelope protein of the HIV-1 virus into mice muscles. The plasmid injection was preceded by treatment with bupivacaine in the same area of the muscle. The authors demonstrated the presence of antibodies capable of neutralizing the HIV-1 virus infection. However, the DNA was injected twice a week for a total of four injections.

Davis et al. (Compte-Rendu du 28 ème Congrès Européen sur le muscle, Bielefeld, Germany, 21-25 Sep. 1992) injected plasmids carrying a luciferase or β-galactosidase gene by pretreating the muscles with sucrose or a cardiotoxin. The authors observed the expression of luciferase or β-galactosidase.

More recently, an article published in Science et Avenir (September 1993, pages 22-25) indicates that Whalen and Davis succeeded in immunizing mice against the hepatitis B virus by injecting pure DNA from the virus into their muscles. An initial injection of snake venom toxin, followed 5 to 10 days later by a DNA injection, is generally described. However, the authors specify that this method is not practical.

These studies were preceded by other experiments in which various DNAs were injected, in particular into muscle tissues. For example, the International application, PCT/US90/01515 (published under No. WO-90/11 092), discloses various plasmid constructions, which can be injected in particular into muscle tissues for the treatment of muscular dystrophy. However, this document specifies that DNA is preferentially injected in liposomes.

Additionally, Canadian patent CA-362.966 30 (published under No. 1,169,793) discloses the intramuscular injection of liposomes containing DNA coding, in particular, for HBs and HBc antigens. The results described in this patent mention the HBs antigen expression. The presence of anti-HBs antibodies was not investigated.

International application PCT/FR92/00898 (published under No. WO-93/06223) discloses viral vectors, which can be conveyed to target cells by blood. These vectors are recognized by the cell receptors, such as the muscle cells, and can be used in the treatment of muscular dystrophy or of thrombosis.

The DNA-based vaccines suggested by the prior art have not been capable of practical uses. For example, some bare DNA used to vaccinate the mice was pure DNA from the virus. This type of treatment can not be considered for human vaccination due to the safety risks involved for the patients. Additionally, earlier experiments in which the injected DNA is contained in liposomes did not exhibit an immune response.

The present inventors have succeeded in developing effective DNA-based immunizing compositions capable of inducing immune responses against infectious viruses without the detrimental effects on human health.

SUMMARY OF THE INVENTION

The present invention relates to a composition capable of inducing T cell response, and more particularly, a cytotoxic response comprising a nucleotide sequence expressed in muscle cells. The nucleotide sequence comprises a gene or complementary DNA coding for at least a portion of a virus protein and a promoter allowing for the expression of the gene or complementary DNA in the muscle cells.

The invention further relates to the vector, which serves as a vehicle for the gene or complementary DNA coding for at least a portion of a virus protein and a promoter allowing for the expression of the gene or cDNA, which is administered to an individual to be immunized.

In addition, the inventors have developed a non-lipid pharmaceutical composition comprising at least, on the one hand, a substance capable of inducing a coagulating necrosis of the muscle fibers, such as bupivacaine, and, on the other hand, a vector including the gene or complementary DNA coding for at least a portion of a virus protein, which is expressed in muscle cells, and the promoter. Preferably, the substance capable of inducing a coagulating necrosis of the muscle fibers is first administered into the muscle of an individual to be immunized. Then, at least five days later, the vector is administered into substantially the same location of the individual's muscle.

The inventors discovered that the compositions of the instant invention are capable of breaking T-cell tolerance to HBsAg in a mouse model for chronic HBV carriers. Thus, the present invention is further directed to the treatment of chronic HBV carriers.

BRIEF DESCRIPTION OF THE DRAWINGS

This invention will be described in greater detail with reference to the drawings in which:

FIGS. 10A to 10C represent the anti-group and anti-subtype ay responses induced by DNA from pCMV-S (DNA) or from the HBS antigen (prot), respectively, in mice B10 (10A), B10S (10B), and B10M (10C).

FIGS. 10D to 10F represent the antigroup responses induced by DNA from pCMV-S (DNA) or from the HBS antigens (prot), respectively in mice B10 (10D), B10S (10E), and B10M (10F).

FIG. 15 describes the expression of HBV sequences in the livers of transgenic and non-transgenic mice. Northern blot analysis of 50 μg of total RNA isolated from the livers of transgenic mice (+) and their non-transgenic littermates (−) after direct injection of DNA (A) or 26 days after adoptive transfer of primed spleen cells (B). $^{32}$P-labelled DNA probes specific for HBV and β-actin were used. The molecular weights (Kb) of the two mRNAs encoded by the transgene are indicated.

A. Lane 1: non-immunized transgenic mouse.
   Lanes 2-4: pCMV-LacZ immunized transgenic mice.
   Lanes 5-9: transgenic mice immunized with pCMV-S2.S DNA.

B. Transgenic mice receiving primed spleen cells harvested from non-transgenic mice 3-6 weeks after immunization with pCMV-LacZ (lanes 2-3) or with pCMV-S2.S (lanes 4-8). Lane 9: transgenic mouse receiving unprimed spleen T cells. Lane 1: RNA from the liver of non-transgenic mouse is shown as a negative control. The transferred spleen cell population is indicated on the top. HBsAg titres (ng/ml) and the present (++) or the absence (−) of HBs antibody at the time of sacrifice are indicated.

Figure 16:
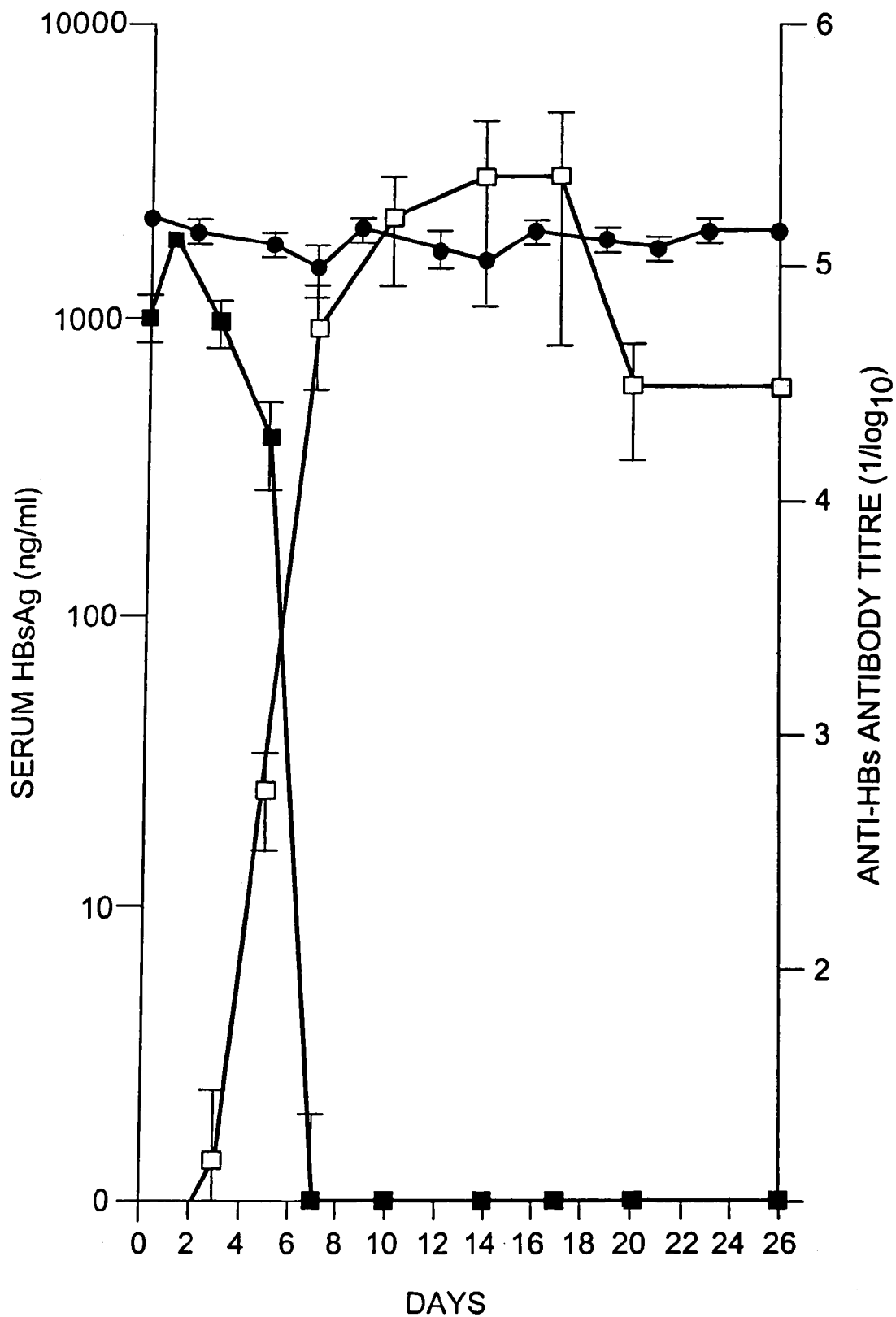

FIG. 16 describes adoptive transfer of primed spleen cells into transgenic mice. Non-transgenic mice were immunized by intramuscular injection of pCMV-S2.S or pCMV-LacZ DNA in order to produce primed spleen cells for adoptive transfer into their transgenic littermates. The mean titre of antibodies in the serum of donor mice at the time of spleen harvest was 1×10$^5$. Eleven pCMV-S2.S recipients were bled at 2 or 3 days intervals and their sera were analyzed for HBsAg (ng/ml)(-■-) and antibodies to HBsAg (-□-), (ELISA, end-point dilution titres). Results are shown as mean titres+/−SEM.

(-●-): Mean titres of serum HBsAg in five control transgenic recipient mice receiving either unprimed pCMV-LacZ-primed spleen cells.

Figure 17:
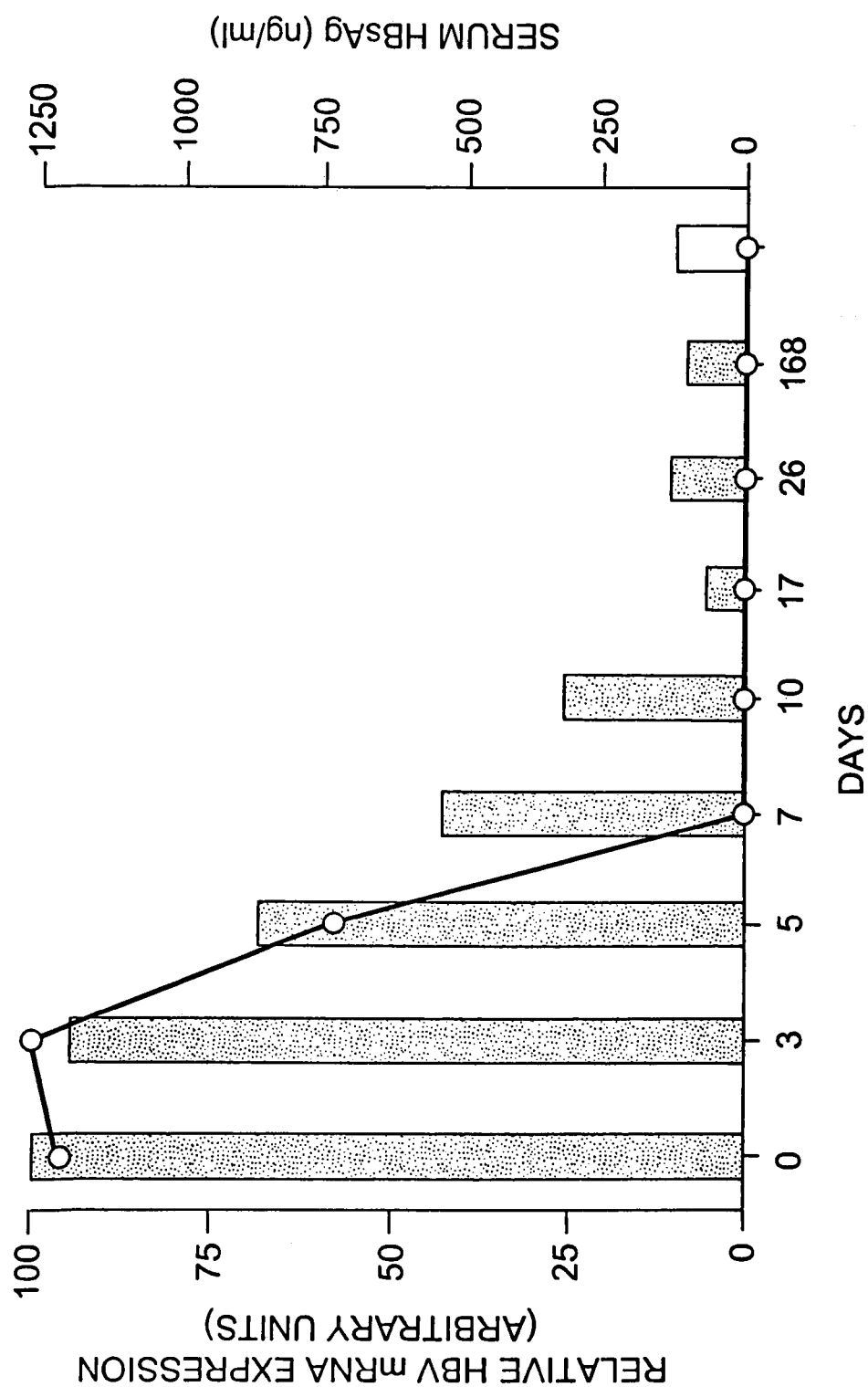

FIG. 17 describes the HBV mRNA content in the livers of transgenic mice taken at various times after adoptive transfer of HBsAg primed spleen cells. Northern blots were performed as in FIG. 15 and the quantitative determination of the HBV mRNA was done by phosphoimager analysis after correction for mRNA loading and variations in transfer efficiency as assessed by β-actin expression. The results are expressed as arbitrary units and represented by grey columns. Background level of hybridization is shown for RNA extracted from a non-transgenic mouse liver (open column on right). Serum-HBsAg concentrations (ng/ml) at the time of liver harvest are shown (-○-).

DETAILED DESCRIPTION OF PREFERRED EMBODIMENTS

The present invention concerns a composition capable of inducing a cytotoxic response against viruses, such as hepatitis B. The composition comprises a nucleotide sequence comprising a gene or complementary DNA coding for at least a portion of a virus protein, wherein said gene or complementary DNA is capable of being expressed in muscle cells, and a promoter. The gene or complementary DNA and the promoter is preferably carried by a vector for administration into an individual to be immunized or treated for infection. The composition is further preferably capable of inducing protective antibodies.

The nucleotide sequence of a gene or complementary DNA may code for at least a portion of a viral protein. Said "at least a portion" of a viral protein signifies, in the context of the invention, an antigenic portion of a protein with which to induce a humoral or cell-mediated immunogenic response, such as a cytotoxic response.

Moreover, the protein can be either a structure protein or a regulatory protein. Preferably, the protein is a structure protein.

In addition, the viral protein may be derived from any infectious virus against which a humoral or cell-mediated immunogenic response is desired. For example, the virus may be a hepatitis virus, such as hepatitis A, hepatitis B, or a non-A, non-B hepatitis virus, such as hepatitis C, E, or delta. Alternatively, the virus may be a non-hepatitis virus, such as HIV-1.

In a preferred embodiment of the invention, the gene or complementary DNA codes for at least a portion of the surface antigen of hepatitis B (HBsAg), particularly, in the S, preS2-S, or preS1-preS2-S form of HBsAg, and where the gene encodes envelope proteins.

Alternatively, the gene made code for HBsAg/ayw.

The gene or protein sequences for hepatitis A, hepatitis B, and non-A, non-B hepatitis viruses, such as hepatitis C, E, or delta, are described by the following documents, which are relied upon and incorporated by reference herein:

French Patent FR 79 21 811;
French Patent FR 80 09 039;
European Patent EP 81 400 634;
French Patent FR 84 03 564;
European Patent EP 91 830 479; and
Najarian et al., Proc. Natl. Acad. Sci. USA, 82:2627-2631 (1985).

Alternatively, the gene or complementary DNA may code for at least a portion of the gp160 protein of HIV-1 virus associated with the p25 protein and/or the p55 protein and/or the p18 protein and/or the Rev protein of HIV-1 virus.

In yet another alternative embodiment, the gene or complementary DNA codes for a protein from a pathogenic microorganism such as the bacterium causing diphtheria, whooping cough, listeriosis, the tetanus toxin, etc.

The promoter is selected for its ability to allow the efficient expression of the gene or complementary DNA in the muscle cells. It may be heterologous, not naturally found in the host, or preferably, homologous, while being originally active in a tissue other than the muscle tissue. The promoter may be an internal or endogenic promoter, i.e., a promoter of the virus from which the gene or cDNA is taken. Such a promoter may be completed by a regulatory element of the muscle or another tissue, in particular, an activating element. Alternatively, the promoter may be from a gene of a cytoskeleton protein, such as that described by Bolmon (J. Submicros. Cytol and Patholog., 22:117-122 (1990)) and Zehnlin (Gene 78:243-254 (1989)). The promoter may alternatively be the promoter from the virus HBV surface genes.

In a preferred embodiment, the promoter is advantageously the promoter for cytomegalovirus (CMV).

The vector of the present invention comprises nucleotide sequence as described above. In particular, the vector comprises the DNA or complementary DNA coding for at least a portion of a virus as defined above and a promoter allowing the expression of the nucleotide sequence in muscle cells.

The vector must be capable of gene transfer of the nucleotide sequence into the muscle cells. In addition, the vector is selected in order to avoid its integration into the cell's DNA, since such integrations are known to activate the oncogens and induce cell canceration. Thus, the vector may be non-replicative.

In an alternative embodiment, the vector may be replicative, which would allow a high number of copies per cell to be obtained and the immune response to be enhanced.

Suitable vectors include but are not limited to plasmids, adenoviral vectors, retroviral vectors, and shuttle vectors. Plasmids are the preferred vector according to the invention.

In a further preferred embodiment, the plasmid is partly bacterial in origin and notably carries a bacterial replication origin. Further preferred is a plasmid carrying a gene allowing for its selection, as is known in the art, such as a gene for resistance to an antibiotic.

The vector may also be provided with a replication origin allowing it to replicate in the muscle cells of its host, as is known in the art, such as the replication origin of the bovine papilloma virus.

In addition, the vector may include a terminal transcription sequence situated downstream of the gene.

The vectors may be obtained by methods known by those having ordinary skill in the art. For example, methods of obtaining these vectors include those by synthesis or by genetic engineering methods. Such methods are described, for example, in the technical manual Maniatis T. et al., *Molecular Cloning, A Laboratory Manual*, Cold Spring Harbour: N.Y. (1982).

Other suitable vectors are described. The pCMV/HBS or pRCCMV-HBS plasmid, having the SEQ ID No. 1 sequence, was filed under No. I-1370 with the Collection Nationale des Cultures des Micro-organismes de l'Institut Pasteur (CNCM) on 21 Oct. 1993.

Additionally, the pRSV/HBS plasmid filed under No. I-1371 with the CNCM on 21 Oct. 1993 is suitable for the instant invention. This plasmid has a similar structure to pCMV/HBS, but includes the Rous sarcoma virus (RSV) promoter instead of the cytomegalovirus (CMV) promoter.

Other plasmids may be:

pCMVHB-S1.S2.S constructed by inserting the fragment BglII-BglII of the S gene, obtained from pCP10, into a pBlueScript vector modified to contain supplementary cloning sites in the "polylinker" portion. The fragment containing the S gene was then removed by KpnI-BssHII digestion then cloned into the corresponding sites of pcDNA 3 (In vitrogen, Rad Systems Europe Ltd, Abingdon UK) so as to obtain pCMVHB-S1.S2.S. This plasmid was filed under No. I-1411 with the CNCM;

pCMVHB-S2.S was obtained by eliminating the pre-S1 part of the HBs gene from pCMVHB-S1.S2.S by KpnI/MstII digestion, then by bonding the two extremities after treatment with 51 nuclease. pCMVHB-S2.S was filed with the CNCM under No. I-1410;

pHBV-S1.S2.S, filed with the CNCM under No. I-1409, was obtained by inserting the S gene BglII-BglII fragment, obtained from pCP10, into a pBlueScript vector modified to contain supplementary cloning sites in the "polylinker" portion;

pBS-SKT-S1.S2.S codes for the three envelope proteins S, S-preS$_1$ and S-preS$_1$-preS$_2$ of the HBV virus; and pSVS codes for the three envelope proteins, S, preS$_2$—S, and preS$_1$-preS$_2$—S of the HBV virus. The construction of the pSVS plasmid is described in EP 0 156 712 B1, which is incorporated herein by reference. Moreover, pSVS has been deposited in the C.N.C.M. under No. I-1840 on Jan. 30, 1997.

The plasmid DNA may be administered in naked form or in a liposome formulation.

The present invention further relates to nucleotide sequences comprising a promoter homologous to the host and another regulatory sequence for the expression of a gene or complementary DNA coding for one of the above-mentioned proteins.

The invention is also directed to a vaccine or medicine containing at least one vector, or a nucleotide sequence, such as defined above. The vaccine or medicine according to the invention is capable of inducing protective antibodies against viruses such as hepatitis B.

Alternatively, the vaccine or medicine according to the invention is capable of inducing a T cell response in chronic HBV carriers. Thus, the invention relates to the treatment of chronic HBV carriers, wherein a composition of the invention is administered into the muscle of the carrier in a therapeutically effective amount.

"Chronic HBV carriers" are defined as individuals, particularly mammals, initially infected by HBV, who fail to resolve their infection. These individuals may remain persistently infected by HBV and do not appear to be capable of eliciting a multispecific polyclonal immune response to several HBV antigens, as compared to those individuals capable of clearing the virus following acute infection. In actively infected chronic patients, the virus replicates in the liver and the disease is mostly mediated by the immune response. Such viral replication is not detected in other individuals.

Large amounts of empty viral particles carrying the HBsAg are produced and secreted by the hepatocytes of chronic HBV carriers. These particles persist in the serum and the corresponding HBsAg-specific antibodies (anti-HBs) are not induced or remain undetectable by the conventional techniques due to the presence of immune complexes. Thus, tolerance to HBsAg is characteristic of chronic HBV carriers.

The present invention relates to breaking the tolerance to HBsAg in order to control the infection. The inventors discovered that the lack of T cell response in a mouse model of chronic HBV carriers may be responsible for this tolerance. Thus, the "treatment" of said chronic HBV carriers relates to the inducement of an immune response to break the T-cell tolerance to HBsAg and a "therapeutically effective amount" is said to be that amount, which induces the immune response to break the T-cell tolerance.

In a preferred embodiment, the composition administered to chronic HBV carriers comprises a plasmid carrying the S2.S form of HBsAg and particularly, is pCMV-S2.S.

The present invention further relates to a composition capable of inducing a cytotoxic response comprised of at least one nucleotide sequence expressed in the muscle cells and a promoter such as defined above.

The present invention further relates to a non-lipid pharmaceutical composition for immunizing an individual against a viral infection, such as a hepatitis, including, on the one hand, a substance capable of inducing a coagulating necrosis of the muscle fibers, such as bupivacaine, and, on the other hand, a vector such as described above or including one of the nucleotide sequences coding for at least a portion of a virus protein, complete or partial, capable of being expressed in muscle cells. The "partial sequence" is a sequence coding for at least six (6) amino acids.

The substance capable of inducing a coagulating necrosis of the muscle fibers is preferably bupivacaine.

The substance capable of inducing a coagulating necrosis of the muscle fibers is administered into the muscle of an individual to be immunized, followed at least five (5) days later by administration of the vector into the muscle of an individual to be immunized. Preferably, the administration of the substance and the vector is substantially in the same location in the individual's muscle. In another preferred embodiment, the vector is administered ten (10) days after administration of bupivacaine and substantially in the same location of the individual's muscle.

The prior administration of bupivacaine has demonstrated an unexpected increase in the effectiveness of the vector administration as well as in the immunization of the individual. Thus, the invention further relates to a method of increasing the effectiveness of DNA-based vaccines, such as those described above.

The compositions of the present invention may contain additives, which are compatible and pharmaceutically acceptable.

Moreover, the compositions of the present invention may be administered by means known in the art and preferentially by intramuscular or intradermal injection. The injection can be carried out using a syringe designed for such use or a liquid jet gun as described by Furth (Anal. Biochem., 205:365-368 (1992)).

The effective amount of bupivacaine used is that which obtains sufficient degeneration of the muscle tissue in order to achieve optimal immunization. An injection dosage of about 0.1 mg to about 10 mg per injected composition is usually suitable.

The effective amount of the vector to be injected is that amount effective to achieve optimal immunization or immunotherapeutic treatment of the individual against the virus of interest according to the protein coded by the gene carried by the vector. An injection dosage of about 0.1 to about 1000 µg of vectors per individual is usually suitable.

The present invention is illustrated by, without in any way being limited to, the following examples.

Example 1

Induction of Antibodies Against a Hepatitis B Surface Antigen by Sequential Injection of Bupivacaine and of a Plasmid Carrying a Gene Coding for the Antigen (1) Materials and Methods 1.1 Bupivacaine Pretreatment All experiments were made on the muscles of the anterior tibia (AT) of mice C57BL/6 aged between 5 to 7 weeks.

A single degeneration-regeneration cycle of the muscle fibers is induced in the muscles of the anterior tibia of non-anaesthetized mice, by intramuscular injection of 50 µl marcaine (bupivacaine 0.5%, DMSO 1%) sold by Laboratoires Astra, France. The solution is injected using a tuberculosis syringe with a needle fitted into a polyethylene sleeve in order to limit the penetration depth to 2 mm.

As marcaine is an anesthetic, injections into the right and left legs were performed at 10 to 30 minute intervals to prevent an overdose.

1.2 DNA Preparation

The plasmid used was constructed by cloning into a modified pBlueScript vector of the XhoI-BglII restriction fragment of the pCP10 plasmid, which contains the gene coding for the HBs surface antigen and the non-translated sequences, both upstream and downstream, including the polyadenylation signal.

The S gene was then recovered by digestion using KpnI-EssHII enzymes and the fragment was cloned into the site of the pRC/CMV vector sold by In Vitrogen. The final plasmid construction was called pCMV-HBS and was filed under No. I-1370 with the CNCM.

Figure 1:
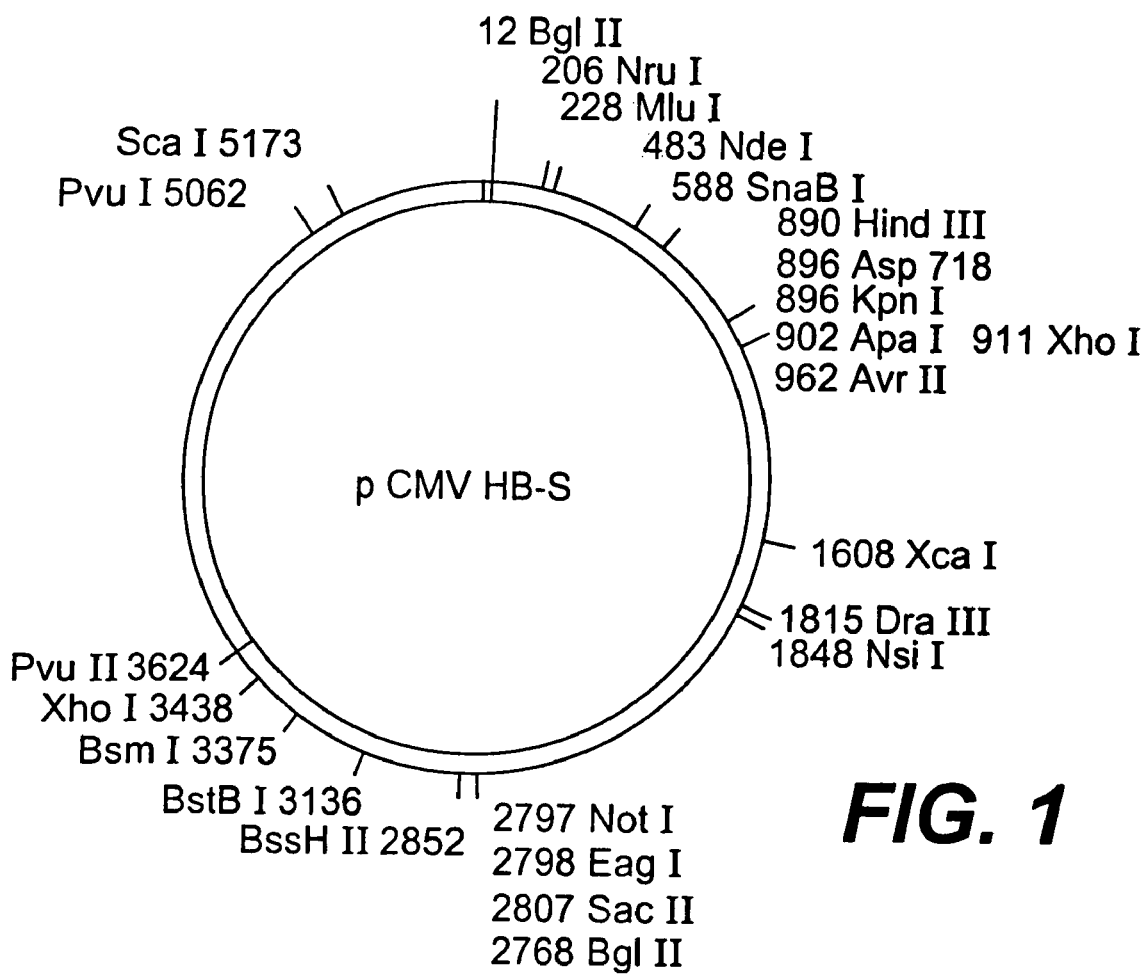
FIG. 1 is a schematic representation of pRC/CMV-HBs plasmid.
Figure 2A:
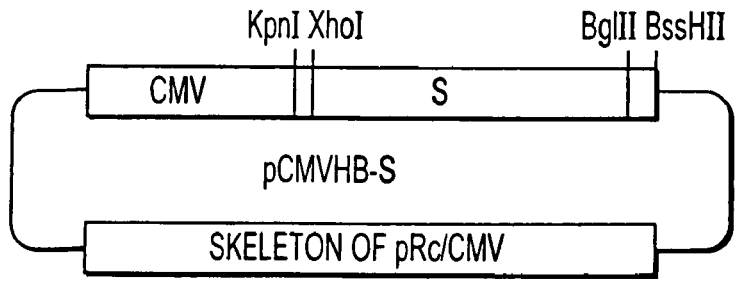
FIGS. 2A to 2D are schematic representations of pCM-VHB-S, pCMVHB-S2.S., pCMVHB-S1.S2.S and pHBV-S1.S2.S plasmids, respectively.
Figure 2B:
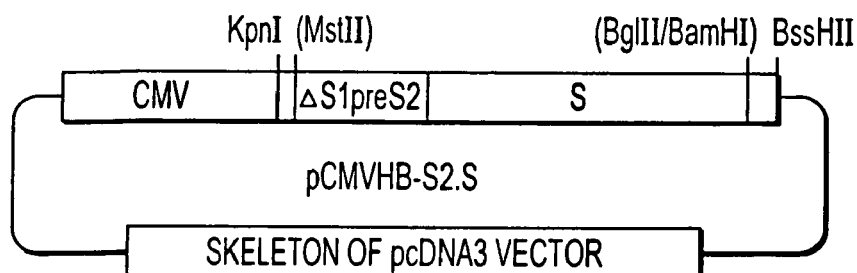
Figure 2C:
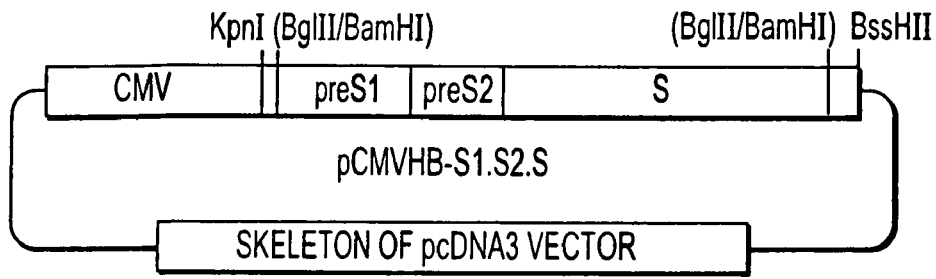
Figure 2D:
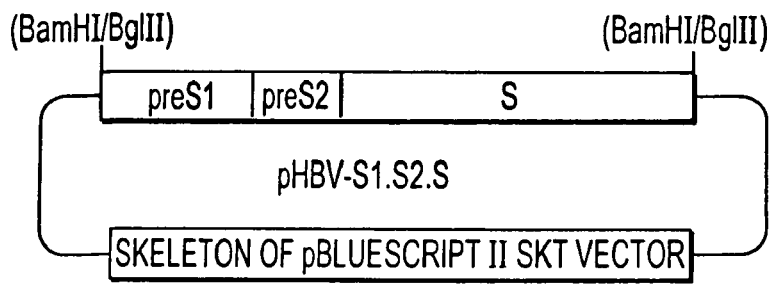
Figure 3:
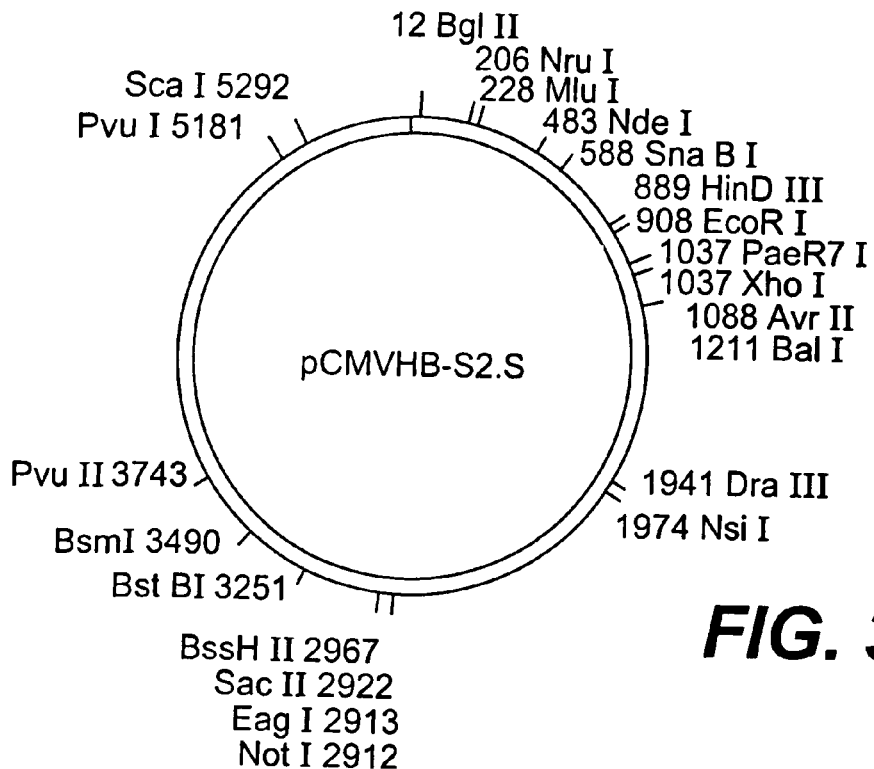
FIGS. 3, 4, and 5 are schematic restriction maps for pCM-VHB-S2.S, pCMVHB-S1.S2.S, and pRSV-HBS plasmids, respectively.
Figure 4:
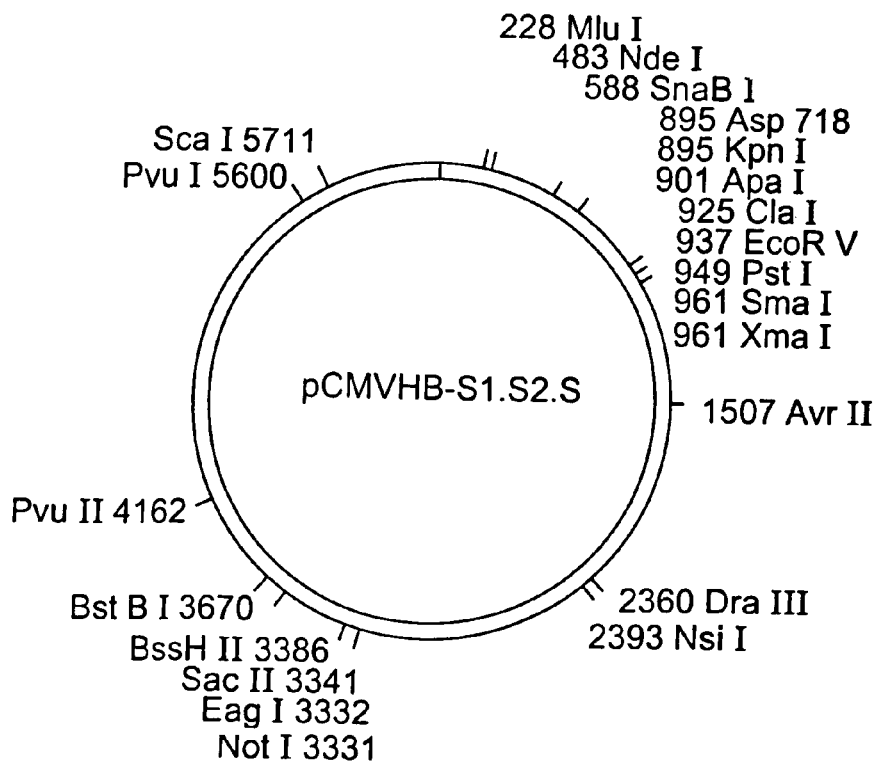
Figure 5:
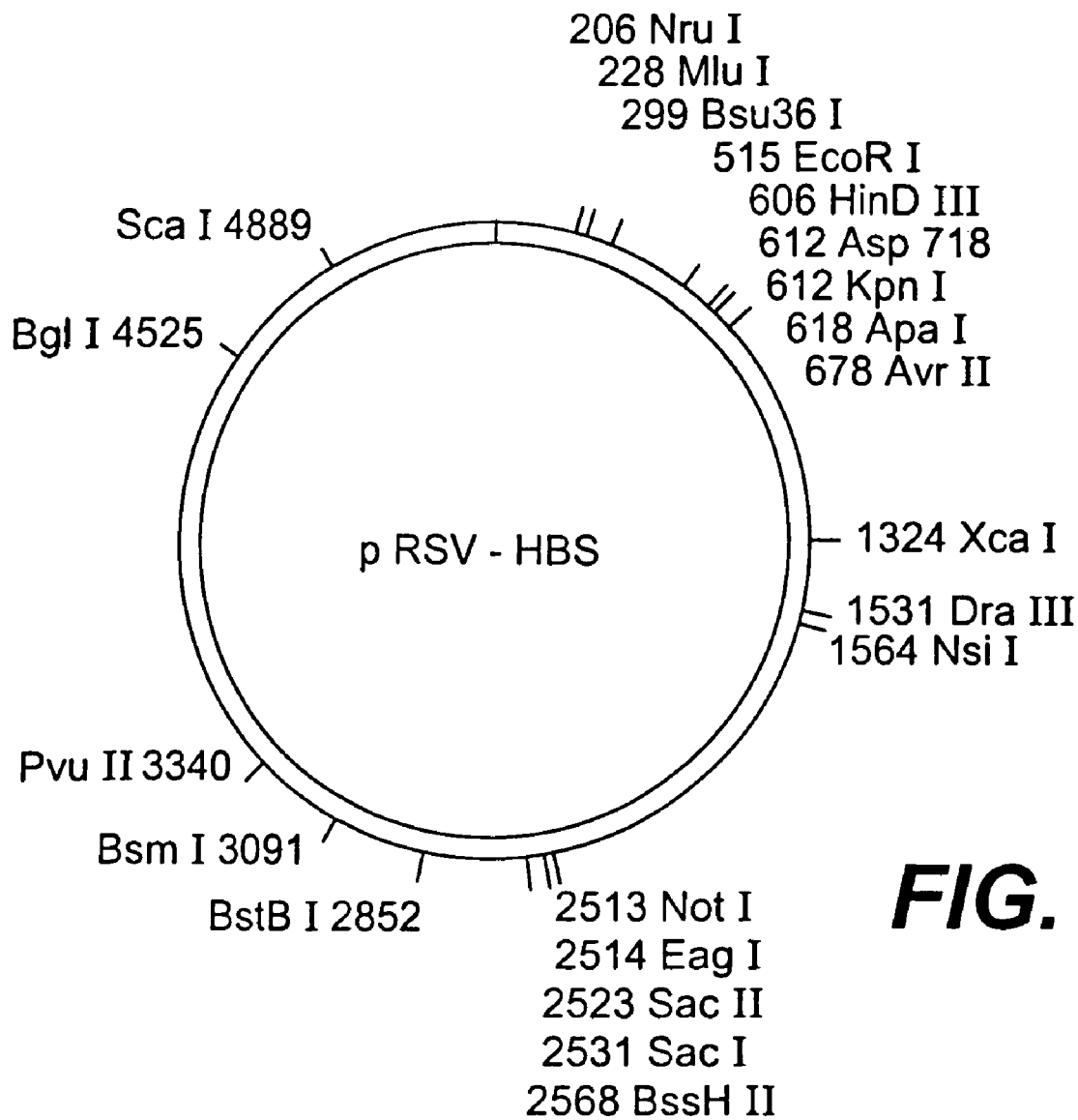
Figure 6:
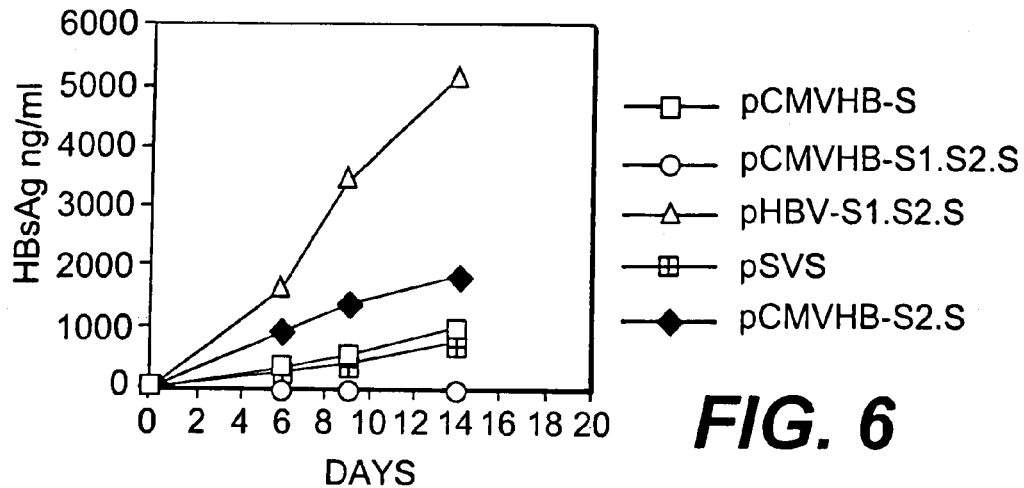
FIG. 6 illustrates the secretion of antigenic HBs particles (HBs Ag) in ng/ml (ordinates) as a function of the number of days (abscissa) for cells carrying the pCMVHB-S, pCM-VHB-S1.S2.S, pHBV-S1.S2.S, pSVS, or pCMVHB-S2.S plasmids.
Figure 7A:
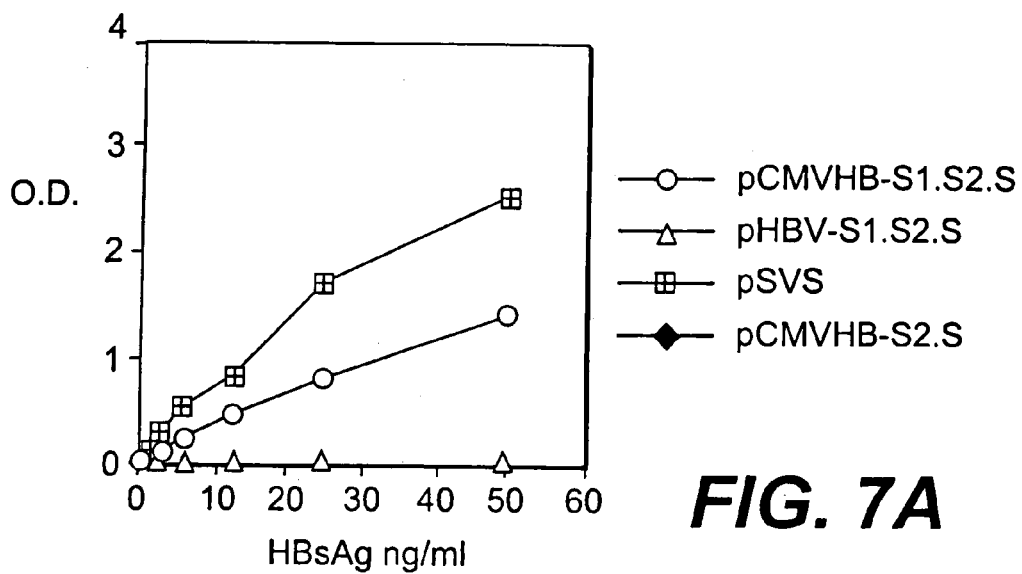
FIGS. 7A and 7B illustrate the determination on some particles in FIG. 6 of the presence of the preS$_1$ and PreS$_2$ antigens using, respectively, anti-preS$_1$, and anti-preS$_2$ antibodies. The formation of antibody-antigen complexes is shown by the optical density (ordinates), as a function of antigen concentration.
Figure 7B:
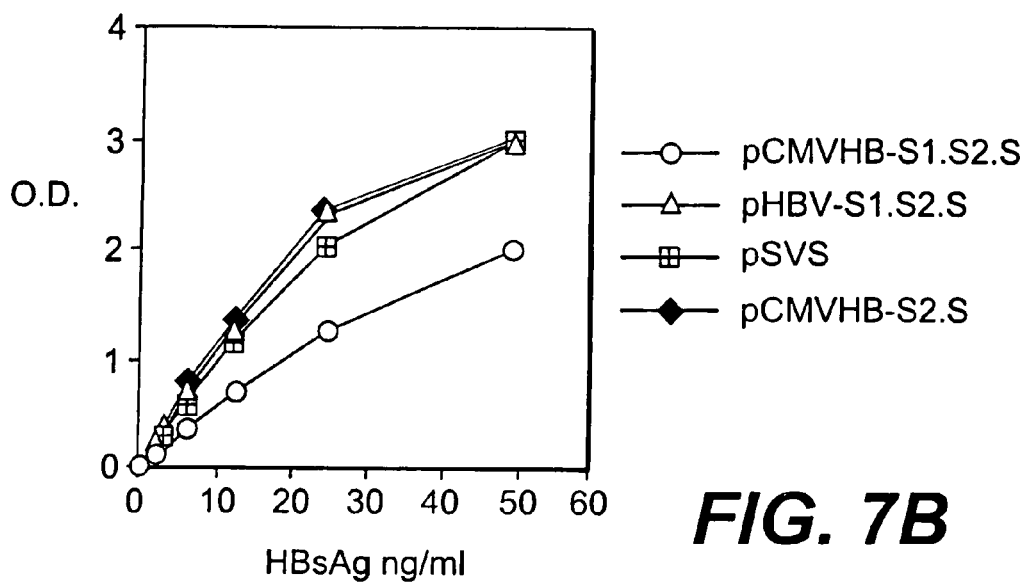

This plasmid is represented schematically in FIG. 1. The CMV promoter is situated between the 288 nucleotide, which is the cleavage position of MluI, and the 896 nucleotide, which is the cleavage position of KpnI. The DNA fragment including the structural gene of the HBs antigen structure was cloned between the 896 and 2852 nucleotides (position of BssH III)

The HBs gene spreads between the 911 (XhoI position) and 2768 nucleotides (BglII position), respectively.

The complete sequence for this plasmid is sequence SEQ ID No. 1.

The purified plasmid DNA was prepared by standard methods then redissolved in PBS buffer and stored at −20° C. until the injection was performed.

1.3 DNA Injection

One to five days after the marcaine injection, DNA was injected into the same area, the mouse being anaesthetized using sodium pentobarbital (75 mg/kg interperitonal path).

The DNA solution, which contains 50 µg of plasmid DNA and 50 µl of PBS buffer, was injected by a single intramuscular injection through the skin into the anterior tibia muscles undergoing regeneration.

The injections were performed bilaterally into the two legs of the mice, each animal thus receiving a total of 100 µg of recombinant plasmid DNA. As for the marcaine injection, the DNA solution was injected using the tuberculosis syringe with the needle described previously.

A single intramuscular DNA injection was performed in each leg.

2. Results

The results obtained are summarized in Table 1 below.

They show very clearly that a DNA injection after treatment with marcaine allows a large number of seric antibodies to be obtained against the hepatitis B surface antigen.

These results are surprising. From the analysis of the state of the art it was not inferred that a plasmid would allow the induction of anti-HBs antibodies, which could be found in the serum and thus allow an effective vaccination.

The ease of application of the plasmid vaccination, and the fact that boosters would not be necessary, allows the consideration of a large scale vaccination.

Example 2

Comparison of the Efficiency of a Plasmid Injection in the Presence and Absence of Lipids A dose of 10 µg plasmid DNA from the SV40-luciferase vector available commercially ("pGL2-Control Vector" from Promega, reference E1 11) in 50 µl of physiological solution was injected into the sucrose pretreated muscle following the method of Davis et al. (Hum. Gene Ther. 4:151-159 (1993)). The injected DNA is mixed earlier with lipids such as dioctadecylamidoglycyl spermine (DOGS) or the following mixtures: DOGS+spermidine, and DOGS+polyethyleneglycol (PEG). The luciferase activity was determined 5 days after the injection.

These results are shown in table II below.

They show that the presence of lipids (DOGS) very significantly reduces the efficiency of the plasmid injection with respect to a composition with no lipids (control).

Example 3

Figure 8A:
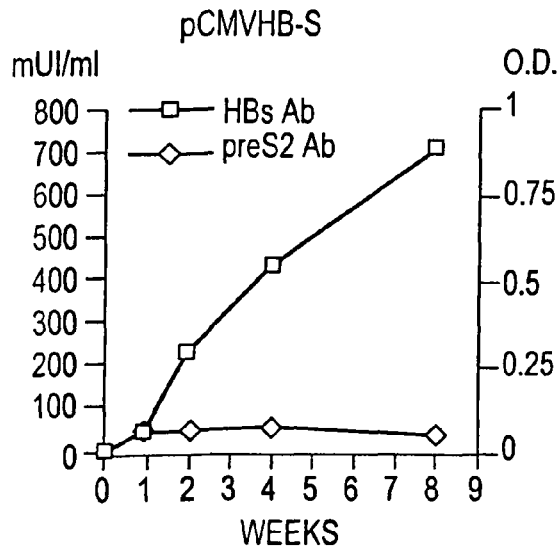
FIGS. 8A to 8D represent the anti-HBS responses (HBS Ab as ordinate, expressed as mUI/ml) and anti-preS2 (preS2 Ab as ordinate, expressed in O.D.) of mice vaccinated by pCMVHB-S (8A), pCMVHB-S2.S (8B), pCMVHB-S1. S2.S (8C), and pHBV-S1.S2.S (8D), respectively.
Figure 8B:
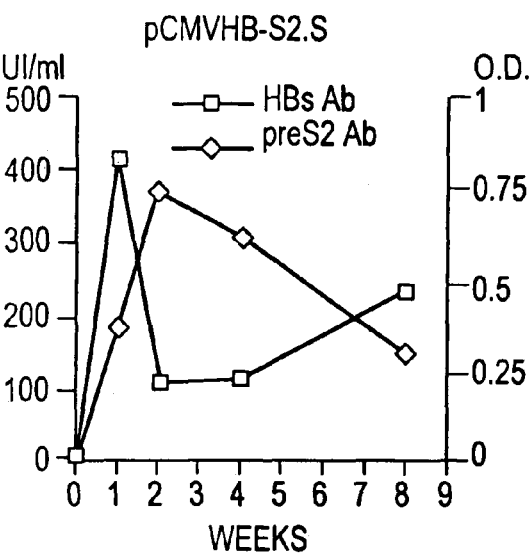
Figure 8C:
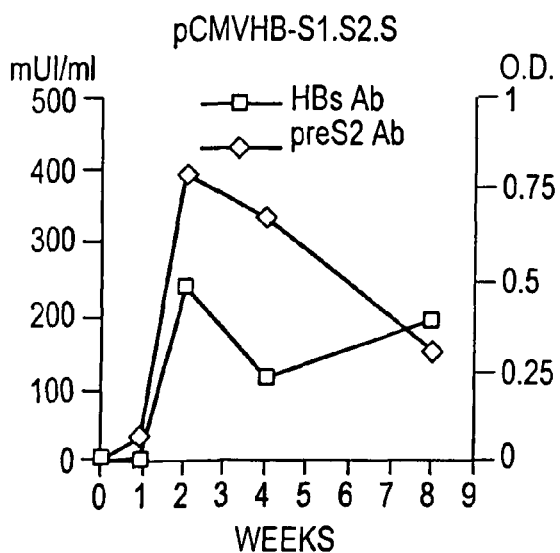
Figure 8D:
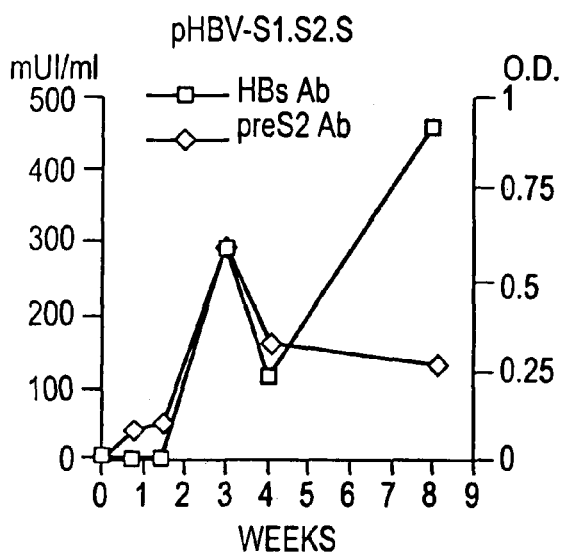
Figure 8F:
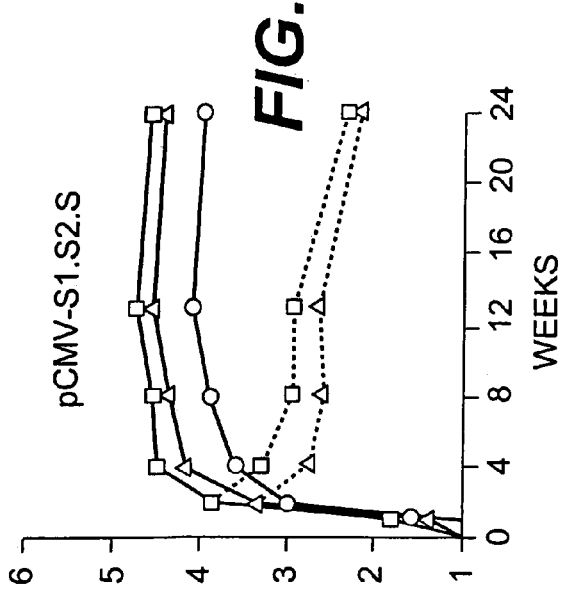
FIGS. 8F and 8G illustrate the kinetics of IgG and IgM anti-HBs in mice immunized with HBV envelope-expressing plasmids. The fine specificity of the antibodies was determined using S-containing HBsAg of a heterologous subtype (ad; circles) of a homologous subtype (ay; triangles), as well as HBsAg containing approximately 30% of the middle (pre-S2 and S) protein of the ay subtype (squares). The bound anti-mouse IgG antibodies are depicted as a continuous line and bound anti-mouse IgM antibodies are depicted as a dotted line.

Comparison of the Responses of Mice and Rabbits to Plasmids Carrying Different Promoters and Envelope Genes for the HBV Virus Five plasmids were constructed allowing the expression of one, two, or three envelope proteins for the HBV virus. In three of the constructions (pCMVHB-S, pCMVHB-S2.S, pCMVHB-S1.S2.S) the genes coding for the HBV virus envelope proteins are put under transcriptional control of the promoter of the CMV virus precursor genes (FIG. 1, FIG. 2A to 2C, FIGS. 3 and 4). The fourth plasmid (pHBV-S1.S2.S) uses the promoter for the HBV virus surface genes contained in the pre-S1 region of this virus (Cattaneo et al. (1983) Nature, 305, 336) (FIG. 2D) as a transcriptional controlling element. In another plasmid, pSVS, the three envelope proteins were placed under control of the SV40 promoter (pSVS) (Michel et al., Proc. Natl. Acad. Sci. USA, 81:7708-7712 (1984)). The construction of the pSVS plasmid is further described in EP0 156 712 B1. In the five constructions, the polyadenylation signal used is contained in the HBV sequences present in 3' of the S gene.

1. In Vitro Control of the Vector Efficiency.

To control the efficiency of these vectors in vitro in eukaryotic cells, mouse fibroblasts or myoblasts were transfected. FIG. 6 illustrates secretion kinetics of HBs particles in the culture supernatants. The low antigen levels produced by transfection of the pCMVHB-S1.S2.S vector are compatible with a large degree of synthesis of the large envelope protein starting from the CMV promoter. This protein being myristilated in its amino terminal region is retained in the endoplasmic reticulum (Ganem, Current Topics in Microbiology and Immunology, 168:61-83 (1991)). Retention in the cell of proteins carrying the pre-S1 determinants was confirmed by immunofluorescence.

The composition of the secreted particles was analyzed in an ELISA sandwich system using as capture antibodies a monoclonal mouse antibody specific to the pre-S1 (FIG. 7A) or pre-S2 (FIG. 7B) determinants and rabbit anti-HBs polyclonal serum as second antibodies. These experiments show that the HBsAg particles produced starting from pCMVHB-S1.S2.S vector carry pre-S1 and pre-S2 determinants showing the presence of the large and medium envelope proteins of the HBV virus. Particles secreted after the transfection of the pCMVHB-S2.S and pHBV-S1.S2.S vectors carry, in addition to the HBs determinants, pre-S2 determinants characteristic of the medium envelope proteins. It was observed that the proportion of pre-S1 and pre-S2 epitopes on the pSVS particles was twice the amount found on pCMV-S1.S2.S HBsAg particles.

2) DNA Inoculation

DNA purified on a Quiagen column was injected by an intramuscular path in a single injection of 100 μg (50 μg/leg) in the anterior tibia muscle of mice C57BL/6 (8 mice per group) Five days prior to the injection, the muscle was pretreated with cardiotoxin in order to induce degeneration followed by regeneration of muscles cells, thus favoring DNA capture by these cells.

The DNA injection experiments were also carried out for rabbits. In this case, pCMVHB-S DNA was administered into normal muscle without degeneration, either by using an injection gun without needle called Biojector®, or by conventional syringes fitted with needles.

3) Anti-Hbs Responses for Mice Vaccinated with DNA

An anti-HBs antibody response is induced by a single injection of any one of the four plasmids used.

The antibody response was analyzed using a commercial anti-HBs antibody detection kit (Monolisa anti-HBs, Diagnostic Pasteur). Anti-preS2 antibodies are detected by an ELISA system using, on the solid phase, a peptide from the pre-S2 (AA 120-145) region corresponding to a B major epitope carried by this area (Neuarth et al., 315:154 (1985)).

FIGS. 8A to 8D illustrate the anti-HBs (HBs-Ab) response kinetics expressed in milli-international units/ml and the anti-pre-S2 response (preS2Ab) determined as optical density (492 nm) for 1/100 diluted serums. Detection was carried out using a mouse anti-immunoglobulin antibody (IgG) labeled with peroxidase.

The injection of the pCMVHB-S plasmid (FIG. 8A) induces a constant anti-HBs antibody synthesis. Seroconversion was observed in 100% of mice from one week after the injection with an antibody average level of 48 mUI/ml (from 12 to 84 mUI/ml, standard deviation (SD)=28), which is 4 to 5, times superior to the threshold required in man to provide protection (10 mUI/ml)

The induced response for a single injection of pCMVHB-S2.S plasmid (FIG. 8B) is characterized by the very early appearance of anti-HBs antibodies. These antibodies reach an average level of 439 mUl/ml (from 104 to 835 mUI/ml; SD=227) at one week then decline before increasing again to reach the initial level at 13 weeks. The significance of this antibody peak will be discussed later. A peak for anti-pre-S2 IgG antibodies is observed at two weeks.

The appearance of anti-HBs antibodies induced by injection of pCMVHBV-S1.S2.S plasmids (FIG. 8C) and pHBV-S1.S2.S (FIG. 8D) is slightly delayed as the mice only seroconvert to 100% after two weeks. The seroconversion profile is identical; it is characterized by an initial response, which is specific to the pre-S2 antigen followed by an anti-HBs response, which gradually increases to reach a level of 488 mUI/ml (from 91 to 1034 mUI/ml; SD=552) (pCMVHBS1.S2.S) and 1725 mUI/ml (from 143 to 6037 mUI/ml; SD=1808)(pHBV-S1.S2.S) at 13 weeks.

Anti-HBs antibodies were not detected earlier than 2 weeks after pSVS injection. However, at its peak level (12 weeks), HBs-specific antibodies induced were two times greater than that with pCMV-S1.S2.S. The sera from mice injected with either pSVS or pCMV-S1.S2.S indicated that they contained both group-specific (a) and subtype-specific (y) antibodies. However, antibodies in pCMV-S1.S2.S-treated mice appeared to show a stronger affinity to pre-S2 than those treated with pSVS.

4) Anti-HBS Response of Rabbits Injected with DNA

Results presented in tables III and IV show that the antibody levels detected at 8 weeks in rabbits immunized using the Biojector are significantly higher than those obtained by a DNA injection by needle.

5) Specificity of Clinically Defined Antibodies

Synthetic peptides were used to determine the relative amounts of pre-S2 and pre-S1-specific antibodies for mice injected with pSVS or pCMV-S1.S2.S. The binding to a synthetic peptide pre-S2 peptide (residues 120-145) or pre-S1 peptide (residues 12-49) was measured and depicted in FIG. 8E. IgM and IgG titers were present after two weeks. While the total titers declined over the next two week, IgG titers continued to increase and was maintained for at least 6 months after DNA injection in mice injected with each vector.

FIGS. 8F and 8G demonstrate that antibodies to other pre-S2 determinants of the middle protein are induced after pCMV-S1.S2.S injection, or alternatively, that the response to pre-S2 is overwhelmed by anti-pre-S1 antibodies in pSVS injected mice.

The peptide encompassing residues 12-49 had previously been shown to bind human antibodies specific to pre-S1 on native HBsAg particles (Milich et al., J. Immunol. 137:315-344 (1986)) and peptide 94-117 to be a dominant antibody binding site for murine antibodies (Milich et al., 1986). Antibodies to pre-S1 peptide 12-4.9, but not to peptide 94-114, were detected in the sera of mice injected with pSVS only. The specificity of the antibody induced suggests that the particles produced after muscle transfection are closely related to particles produced in vivo during infection in humans.

Figure 8H:
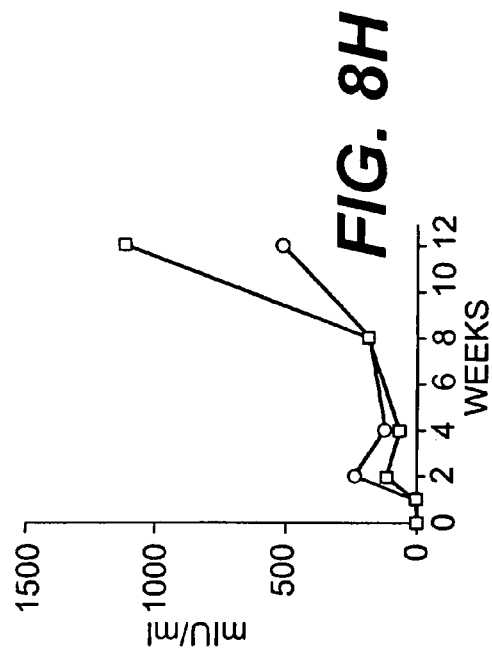
FIG. 8H depicts the anti-HBs immune response in mice injected with the two expression vectors pSVS (squares) and pCMV-S1.S2.S (circles).
Figure 8E:
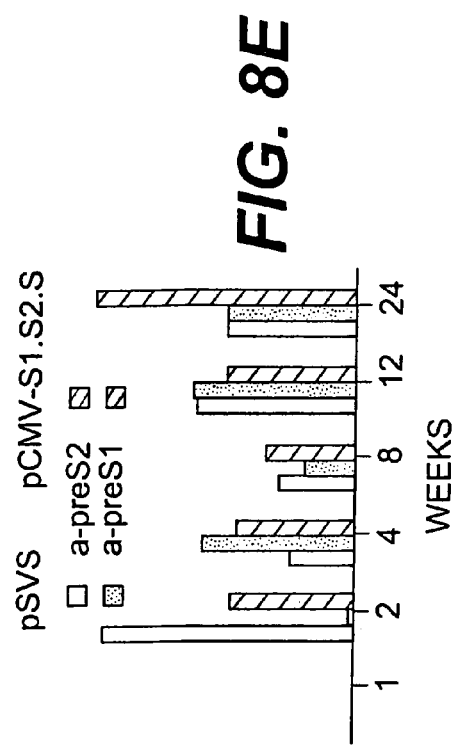
FIG. 8E depicts the kinetics of appearance of anti-pre-S2 and anti-pre-S1 antibodies in sera from groups of mice injected with HBV envelope-expressing plasmids (pSVS and pCMVS1S2S).
Figure 8G:
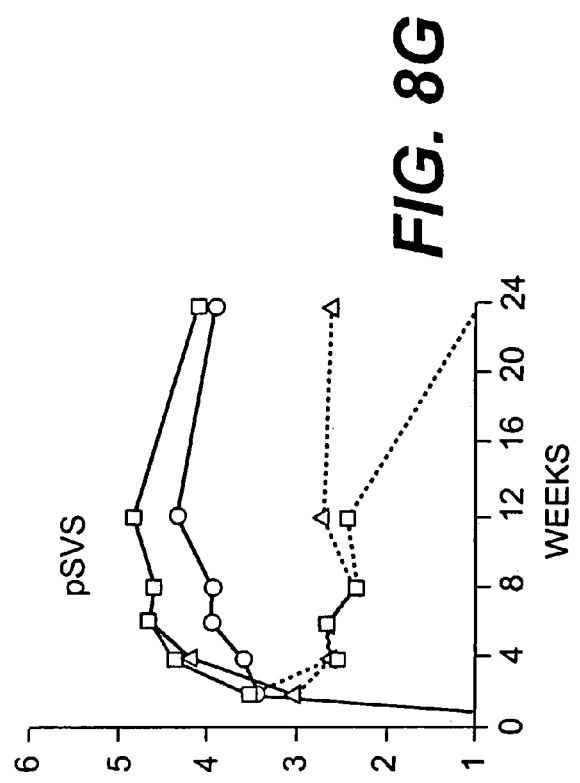

FIG. 8H depicts the antibody levels in mice injected with expression vectors pSVS (squares) and pCMV-S1.S2.S (circles). After two weeks of DNA injection, 100% of the injected mice had seroconverted to a titer of at least 10 mIU/ml, which is recognized as a level to be protective in humans. At 12 weeks, these levels were 50 to 100 times higher.

Example 4

Humoral Responses of Mice to Genetic Vaccine

1) Qualitative Analysis of the Humoral Response

ELISA systems applied to the solid phase of the HBs antigens of varying composition with respect to the determinants presented on the solid phase and using mouse antibodies specific to IgM or IgG as second antibodies gave a qualitative analysis of the antibody response that was achieved.

In all cases, the single injection of DNA in mice is characterized by the early appearance of HBsAg specific to IgM followed immediately by conversion to IgG isotype antibodies, which is characteristic of the memory response induced by the auxiliary T cells. The antibody response to the DNA injection is characterized by its prematurity. Indeed, seroconversion is achieved 8 to 15 days after the injection depending on the DNA type used and in all cases the plateau is achieved in four weeks and maintained constantly over a period of 12 weeks.

The use of the heterologous subtype HBs antigens (ad) fixed on ELISA plates allows the formation/detection of the presence, in the serum of immunized mice, of antibodies specific to the anti-a group, and by difference in reactivity with respect to HBsAg of the same subtype (ay), of antibodies specific to the anti-y subtype. The presence of antibodies specific to determinants of the HBsAg group is very important as the former are capable of giving protection against the heterologous subtype virus during virulent tests in chimpanzees (Szmuness et al., N. Engl. J. Med. 307:1981-1486 (1982)).

Figure 9:
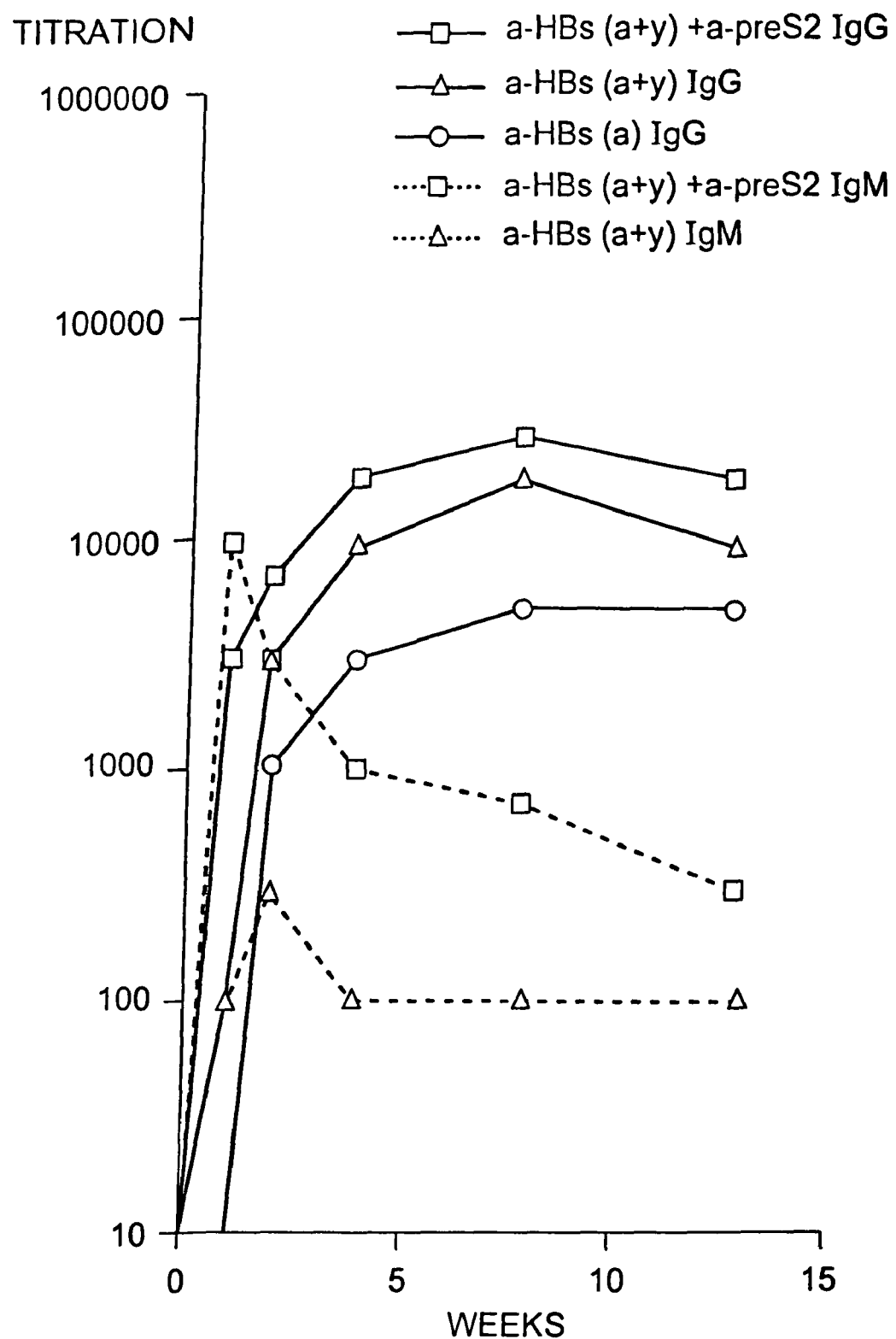
FIG. 9 illustrates the antibody response, IgG and IgM immunoglobulins (titre as ordinates), of a mouse vaccinated by pCMVHB-S2.S as a function of the number of weeks (abscissa).
Figure 11:
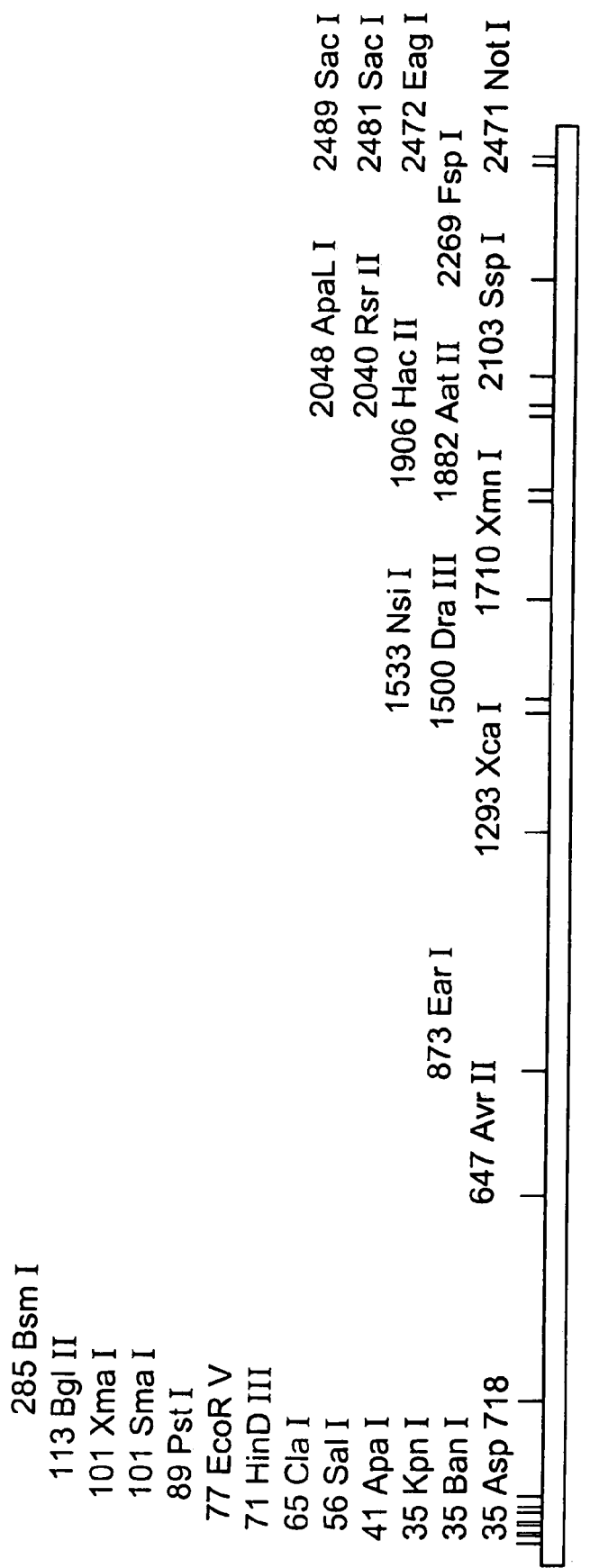
FIG. 11 represents a linear restriction map for the pBS-SKT-S1.S2.S plasmid.

Analysis of the response induced by the pCMV-S2.S vector shows that it has a remarkable similarity with the one, which can be observed in man during infection. It is characterized by an extremely early (8 days) peak for IgM which is specific to the pre-S2 region immediately followed by conversion to anti-pre-S2 IgG (FIG. 9). This response is followed by the appearance of IgM then IgG anti-HBs antibodies. The anti-HBs antibody production is constant and reaches a maximum after 4 weeks. At 13 weeks IgG anti-HBs and anti-pre-S2 remain at a constant level.

The anti-subtype (y) response precedes that of the anti-group response (a) in the same way as that described for the vaccination with the recombinant vaccine (Tron et al., J. Infect. Dis. 160:199-204).

Thus, injection of a vector encoding the small and the middle forms of HBV envelope protein (pCMV-S2.S) into normal mice induced a strong and long-lasting humoral response to the preS2 domain of the middle protein and to subtype and group-specific HBsAg determinants.

The response obtained with the three other DNA vaccines illustrates the commutation of class IgM-IgG, which is characteristic of the secondary response.

The response being first of all directed against the subtype before being against the HBsAg group determinants.

The long term response, which was studied for pCMVHB-S DNA, shows that the antibody peak is reached within 3 months and this remains at a constant level 6 months later (Table V) (Davis et al., Vaccine, 14(9):910-915 (1996)).

2. Immunization of Mice with Genetic Vaccine and Non-Response

The high number of non-responders to the classical vaccine (2.5 to 5%) remains a major problem for vaccination against hepatitis B. It has been possible to correlate the non-response in man to certain HLA types (Krustall et al., J. Exp. Med. 175: 495-502 (1992)) and to a defect in the antigen presentation or stimulation of the auxiliary T cells.

To study the possible impact of the genetic vaccination on the HBsAg non-response, a range of mice strains that were used for which the response to various HBV virus envelope proteins is controlled genetically and has been well characterized by Millich et al. (J. Immunol. 137:315 (1986)). The pCMVHB-S construction previously described was injected into B10 ($H-2^f$), B10.S($H-2^s$), and B10.M ($H-2^f$) mice muscles.

The B10 strain responds to the three virus envelope proteins. The B10.S strain does not respond to HBsAg, however this non-response can be overcome by immunization with HBsAg antigens which are carrying pre-S2 determinants. The B10M strain is totally non-responsive to both HBs and pre-S2 antigens. A response for the latter strain can be achieved by immunization using HBsAg carrying pre-S1 determinants.

The mice immunized by the DNA received a single injection (100 µg) in the regenerating muscle. Control mice were injected with two intraperitoneal injections of protein at an interval of one month, the first of 2 µg HBsAg to which the complete Freund additive (CFA) was added and the second of 2 µg HBsAg to which the incomplete Freund additive (IFA) was added.

The results obtained for pCMVHB-S are illustrated by FIGS. 10A to 10F.

In the B10 strain (good responder), the DNA-induced response is earlier than that induced by the protein after a single injection.

The appearance of anti-HBs antibodies subtype specific then group specific after immunization with pCMVHB-S DNA was observed in the B10S strain (nonresponder to HBsAg in the absence of pre-S2). Group specific anti-HBs antibodies are observed in HBs protein immunized mice only after the second injection.

A group and subtype specific anti-HBs response is obtained for DNA immunization of strain B10M (nonresponder to HBsAg in absence of pre-S1), whereas only a subtype specific response is induced by the protein with two injections being required.

The response induced by the three vector types is compared in the three mice strains.

3. Genetic Vaccine in HBsAG Transgenic Mice

Figure 12:
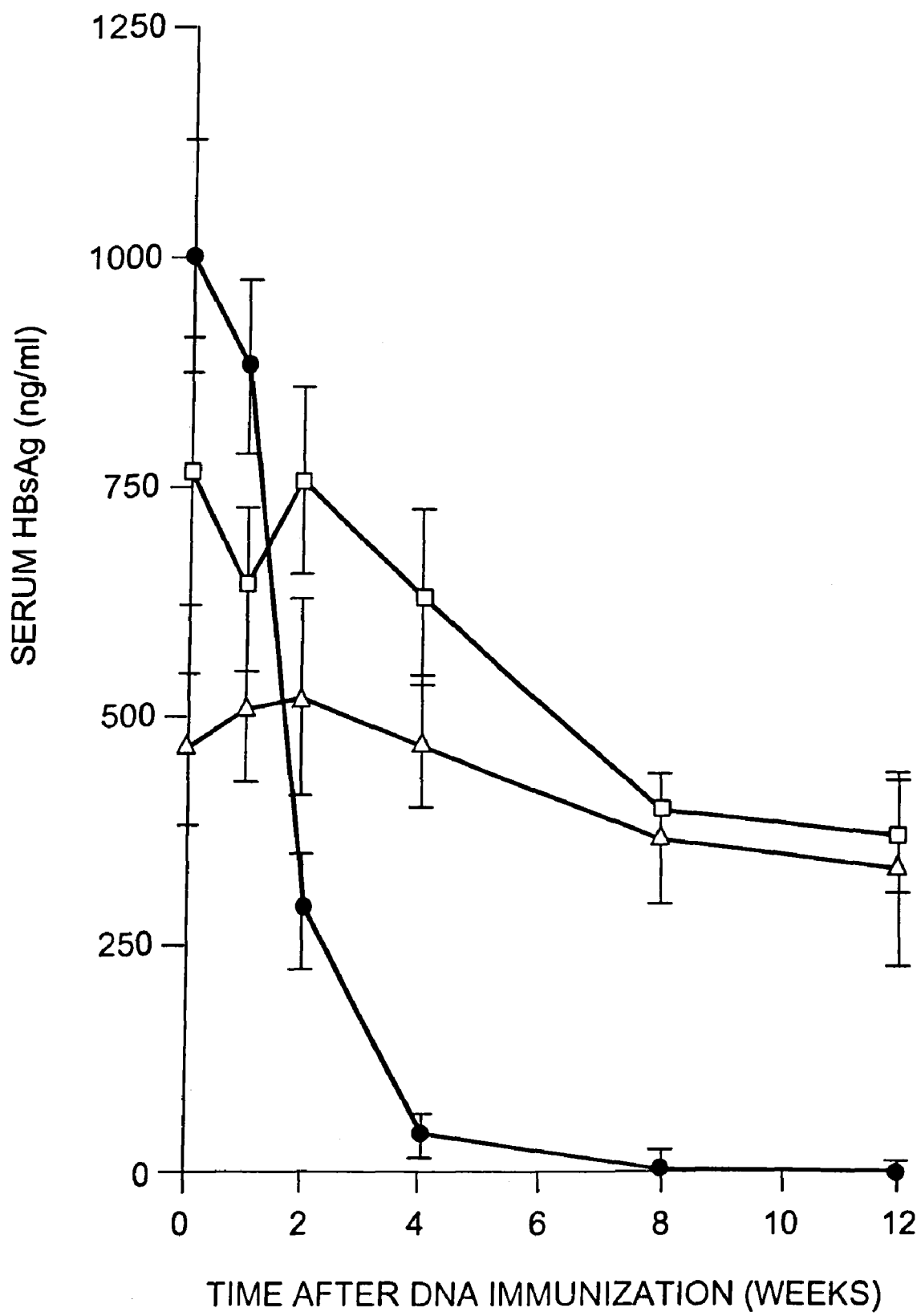
FIG. 12 represents the DNA-based immunization of transgenic mice. Groups of 6 female transgenic mice were immunized once by intramuscular injection of 100 µg of the DNA plasmid pCMV-S2.S (-●-) or pCMV-LacZ (-□-) five days after cardiotoxin treatment. A group of 8 transgenic mice were injected with PBS instead of DNA (non-immunized controls (-Δ-). Mice were bled at weekly intervals and the sera were analyzed for HBsAg (expressed as ng/ml). Each point represents the mean titre for the group and error bars represent the standard errors of the mean.
Figure 13:
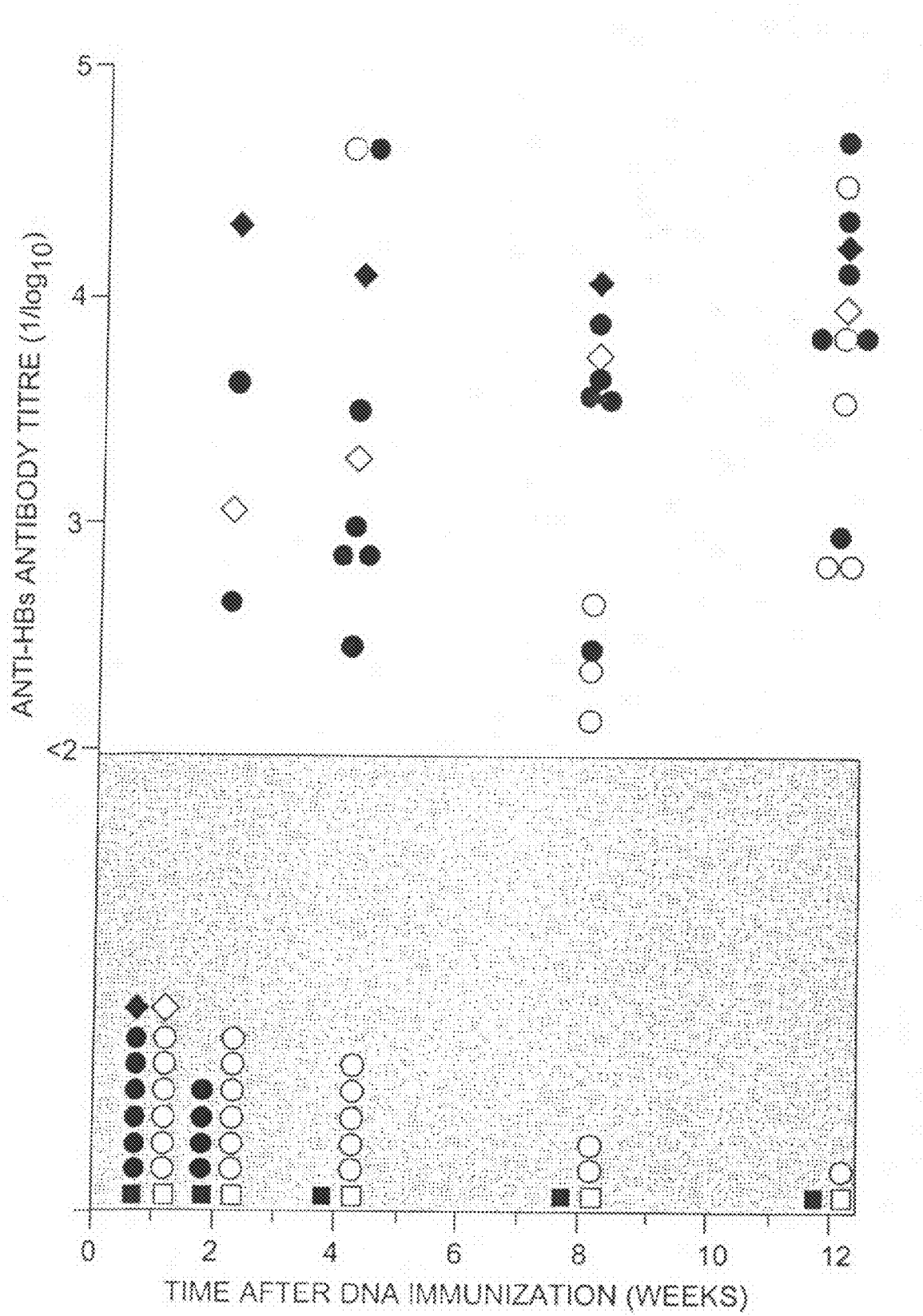
FIG. 13 describes the kinetics of appearance of anti-HBs antibodies in mice following injection of pCMV-S2.S DNA. Sera were taken as in FIG. 12 and the fine specificity of the antibodies was determined using HBsAg particles containing either the S (open symbols) or the S plus preS2 proteins (filled symbols). Anti-HBs antibodies (Ig) were expressed as $1/\log_{10}$ of the antibody titre (determined by serial end-point dilution analysis). Circles represent the immunized transgenic mice shown in FIG. 1, diamonds are non-transgenic immunized mice, and squares are transgenic mice injected with pCMV-LacZ. Symbols in the grey area correspond to mice which gave no detectable seroconversion (titre<100).

Transgenic mice of the C57BL/6 strain is used as a model of chronic HBV carriers since they constitutively express HBsAg. A single injection of the pCMV-S2.S DNA into HBsAg-transgenic mice (H-$2^b$) provoked a decrease in titres of circulating HBsAg (FIG. 12) and the concomitant appearance of anti-HBs antibodies, which increased over time (FIG. 13). In some of the mice, antigen was eliminated from the serum as early as four weeks after injection of the DNA and remained undetectable for at least twelve weeks without further injections of DNA. In the remaining mice, antigen levels also fell and were maintained at low levels. These effects were not due to non-specific immune stimulation induced by the injection procedure or the presence of DNA per se, since HBsAg levels were unaffected (FIG. 12) and no anti-HBs were detected (FIG. 13) in control transgenic mice injected with PBS alone or a DNA vector expressing beta-galactosidase (β-gal; pCMV-LacZ) (Davis, 1993), even though the latter procedure induced high levels of anti-B-gal antibodies (ELISA titres>$10^5$ by 12 weeks post immunization).

Figure 14:
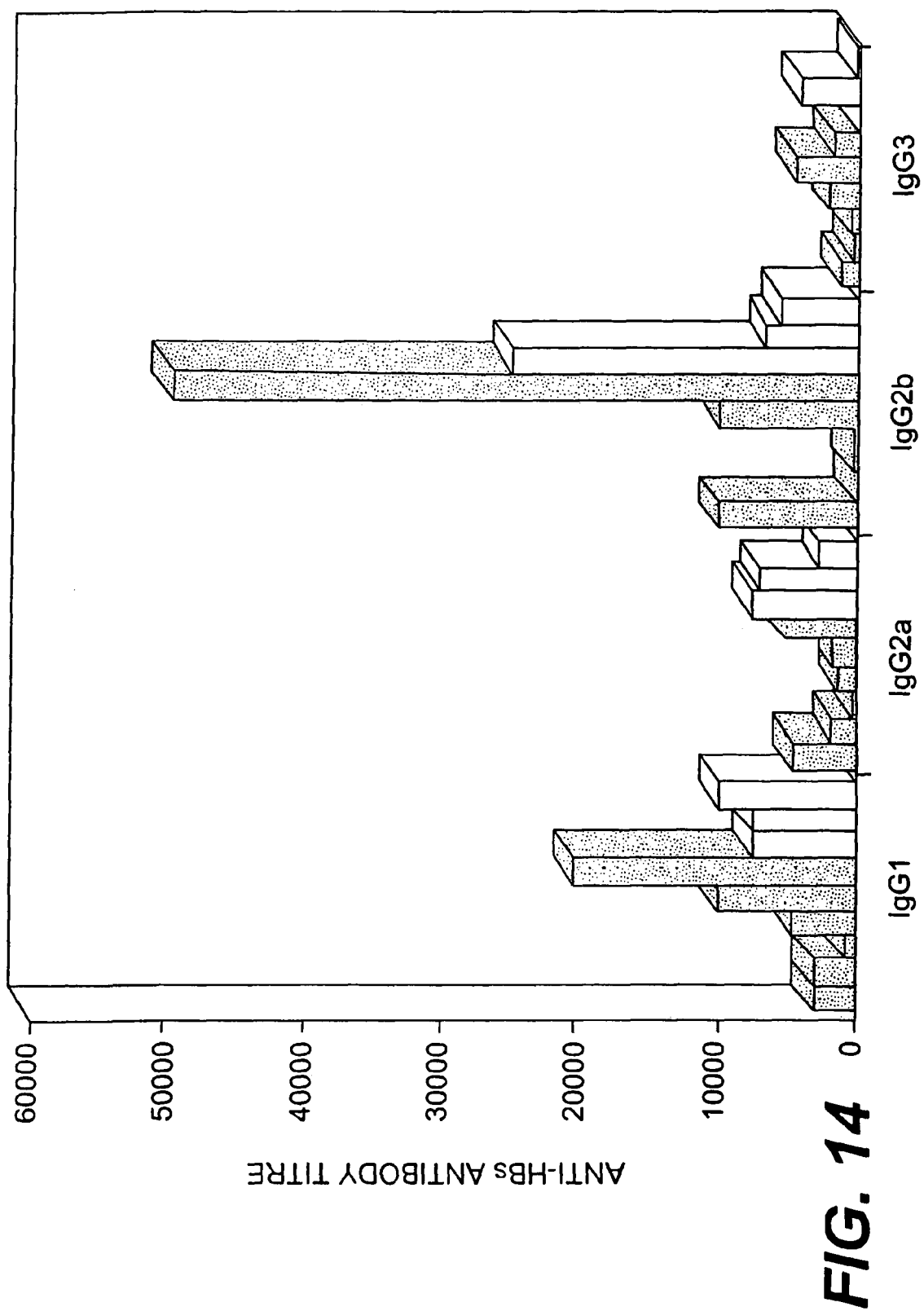
FIG. 14 provides an anti-HBs IgG isotype profile in the sera of six individual transgenic mice (solid columns) and three non-transgenic mice (open columns) at 12 weeks after immunization with pCMV-S2.S DNA. HBsAg-specific IgG1, IgG2a, IgG2b, and IgG3 antibodies were detected by ELISA with specific secondary antibodies. Antibody titres are expressed as a serial end-point dilutions, which was defined as the highest serum dilution that resulted in an absorbance value two times greater than that of non-immune or control serum, with a cutoff value of 0.05.

Free antibodies were first detectable in the plasma of transgenic mice 2-4 weeks following a single injection of pCMV-S2.S DNA (FIG. 13). The first antibodies detected were preS2-specific since they reacted only with particles carrying this epitope but not with particles devoid of it. Anti-HBs antibodies were not observed until 8 weeks, at which time there was a complete clearance of circulating HBsAg (see FIG. 12). It is remarkable that, even though the transgenic mice had been tolerant to high levels of circulating HBsAg, DNA-based immunization was able to induce titres of anti-HBs comparable to those induced in non-transgenic controls, and that these antibodies were able to completely neutralize the circulating HBsAg. The isotype profile of the anti-HBs antibodies was identical in transgenic and in non-transgenic mice and included IgG2 as well as IgG1 with some IgG3 (FIG. 14). Such isotype switching of autoreactive B cells strongly suggests that the DNA-mediated immunization triggered CD4+T helper cells.

3.a. Cytokine Production from Spleen Cells of Transgenic and Non-Transgenic Mice To further characterize the T-helper subset, the cytokine production from spleen cells in culture was analyzed. Spleens were removed from transgenic mice 20 weeks after DNA injection and cell suspensions were specifically stimulated in vitro with HBsAg. These cultures produced γ-interferon (IFN-γ), low levels of IL-2 and TNF-α, but no IL-4 as depicted in Table VII. The secretion of IgG2a and γ-interferon is consistent with a predominant Th1 response, however, detection of IgG1 suggests that the Th2 response was also induced.

3.b. Regulation of Transgene Expression in pCMV-S2.S Vaccinated Transgenic Mice The rapid clearance of circulating antigen from immunized mice did not appear to result from a significant or persistent HBsAg-specific cytopathic effect on the liver since levels of transaminase activity in the plasma remained normal subsequent to injection of DNA and histological examination of the liver at the time of HBsAg clearance showed not evidence of necrosis or inflammation (not shown).

Since the inventors could not correlate the persistent clearance of the transgene product with any apparent destruction of the transgene-expressing liver cells, the HBV mRNA content in the livers of transgenic B10 mice was evaluated. At 12 weeks after immunization with pCMB-S2.S, the mRNA was decreased in the livers of those mice which had partially cleared the antigen, and was undetectable in those which had completely eliminated HBsAg from their sera (FIG. 15A, lanes 5 and 6-7 respectively). This effect is persistent since HBV mRNA remained undetectable in the livers of mice analyzed 20 weeks after DNA injection (FIG. 15A, lanes 8-9). In contrast, HBV mRNA was not diminished in livers taken from untreated transgenic mice or control transgenic mice, which had been injected with pCMV-LacZ DNA (FIG. 15A, lane 1 and lanes 2-4 respectively). This indicates that the inhibition of viral gene expression in transgenic mice injected with pCMV-S2.S was not due to anon-specific effect such as the release of cytokines with injection-induced inflammation and/or with an immune response against transfected muscle cells expressing a foreign antigen (i.e., β-gal). Thus, the HBsAg-specific immune response induced by immunization with plasmid DNA appears to be responsible for controlling hepatic transgene expression by some non-cytopathic mechanism.

3.c. Injection of DNA Induced B and T-Cell Response to HbsAg

To determine which component of the immune response is implicated in the down-regulation of HBV-specific mRNA and in the observed decrease or elimination of the circulating antigen, adoptive transfer experiments were performed. Fully immunocompetent non-transgenic mice were immunized once with the pCMV-S2.S DNA vector and when ELISA titres of serum antibodies to HBsAg had reached at least $10^4$, both the serum and the primed spleen cells were harvested from the mice for transfer into their transgenic littermates.

Passive transfer of serum-derived antibodies on a single occasion into transgenic mice induced a rapid but transient decrease in circulating HBsAg levels (mice 2.21 and 4.2.6, Table VI). In other transgenic mice, circulating antigen was maintained at undetectable levels for a longer period by intraperitoneal injection of hyperimmune sera every 2-3 days over a period of 17 days (mice 1.3.5 and 1.3.6, Table 2). Neither single nor chronic administration of antibodies resulted in decreased HBV-specific mRNA in the liver (not shown) indicating that the humoral response after DNA-based immunization was not responsible for the down-regulation of transgene expression or the long-term elimination of the transgene product.

Injection of primed spleen cell suspensions obtained from pCMV-S2.S immunized non-transgenic donor mice into transgenic littermate recipients resulted in a rapid clearance of circulating HBsAg (by 7 days) and a concomitant appearance of anti-HBs antibodies, which were sustained (FIG. 16). This indicates that the transferred T and B cells were functional within the environment of the transgenic mice and that the B cells were activated, probably by the circulating antigen. Adoptive transfer of HBsAg-primed spleen cells was also able to induce a complete disappearance of HBV mRNA in the liver by 17 days (FIG. 17 and FIG. 15B, lanes 4, 5). The inability to detect serum HBsAg occurred 10 days prior to the disappearance of HBV mRNA suggesting that two separate mechanisms may be responsible for the observed clearance of the antigen: an initial transient elimination due to formation of immune complexes and a subsequent more permanent control of transgene transcription. Serum transaminase activity and histological examination of liver sections were monitored every 2-3 days after adoptive transfer and found to be normal for up to 17 days, after which some histological sections of liver exhibited a few small necrotic foci. These were sometimes accompanied by the presence of inflammatory cells, but in no case did the necrotic regions involve more that 5% of the hepatic cells. In addition, a few apoptotic hepatocytes were detected in centrilobular areas within some randomly distributed lobules (not shown). The changes induced by adoptive transfer with HBsAg-primed spleen cells were HBsAg-specific since injection of β-gal-primed spleen cells into transgenic recipients had no effect on the levels of serum HBsAg (FIG. 16) or liver HBV mRNA (FIG. 14B, lanes 2,3).

3.d. T Cells are Able to Control Transgene Expression in the Absence of Antibody Production.

To determine the spleen cell population, which was involved in the decrease or disappearance of circulating HBsAg and liver HBV mRNA, adoptive transfer was carried out with fractionated B- or T-spleen cells obtained from non-transgenic donor mice immunized with pCMV-S2.S. After depletion of T-cells, the transfer of HBsAg-primed spleen cells into transgenic mice did not induce anti-HBs and had no effect on levels of circulating HBsAg or liver HBV mRNA (FIG. 15B, lane 6). This indicates that antibody production in DNA-immunized transgenic mice is T-cell dependent. In contrast, transfer of B cell-depleted spleen cells resulted in clearance of circulating HBsAg within 14-17 days although antibody to HBsAg was not detected in these recipient mice at these or later times (not shown). Thus, antigen-antibody complex formation is not required for, but has a synergistic effect on the elimination of circulating antigen (FIG. 16). Furthermore, it appears that HBsAg-specific T cells are also responsible for down regulation of transgene expression since only transfer of T- but not B- or unprimed T-cells was able to reduce HBV mRNA in the liver to undetectable levels (FIG. 15B, lane 6-9).

4. Genetic Vaccine in Clinical Trials

H. A. Thoma, Progress in Hepatitis B Immunization, P. Coursaget and M. J. Thong (Eds.), Colloque INSERM: Paris, France, 194:35-42 (May 3-5, 1990), the entire contents of which are incorporated by reference herein, reports that a third generation vaccine containing portions of pre-S1, pre-S2, and S proteins demonstrates fast and high immune response in clinical trials in man as compared to other available vaccines.

It is generally thought that the humoral response to HBs antigens is sufficient by itself to give protection. The presence of antibodies directed against other determinants (pre-S1 and pre-S2) carried by the virus envelope proteins, themselves protectors, could improve the response quality. The experiments reported here as a whole illustrates that the humoral response induced by the genetic anti-hepatitis B vaccination is greater in several fields than that which can be achieved for the classical vaccination.

In terms of seroconversion levels, the 100% level is obtained, after only one injection, from day 8 for mice immunized with pCMV-HBS DNA and pCMVHB-S2.S.

In terms of response level, the 10 mUI/ml threshold level, considered sufficient to give protection in man, is always greatly exceeded.

In terms of the speed of response, in 8 days a very high level of anti-pre-S2 antibodies is obtained for the pCMVHB-S2.S vector and it is known that the former are capable of giving protection by themselves (Itoh et al., (1986) Proc. Natl. Acad. Sci. USA 83, 9174-9178).

In terms of response stability, anti-HBs antibodies remain constant at a high level for more than 6 months.

In terms of response quality, type IgG antibodies characteristic of a response, which is dependent on the auxiliary T cells and therefore on a memory response, are obtained. Moreover, the single injection of DNA encoding the HBV protein is sufficient to break T-cell tolerance in transgenic mice expressing the same envelope sequences in the liver.

In terms of anti-viral activity, the antibodies are specific to the viral subtype, but especially group-specific and therefore susceptible to giving a cross protection and to clear HBsAg particles in HBsAg transgenic mice.

In terms of biological significance, the response profile obtained by pCMVHB-S2.S immunization mimes totally that which is observed in man after a resolved viral infection.

The immune response resulting from plasmid expression of the HBsAg leads to both clearance of circulating antigen as well as the induction of T-cell responses capable of suppressing HBV mRNA accumulation in the liver in a transgenic mouse model. Despite the high concentration of transgene product in the circulation, auto-antibodies are induced soon after DNA injection, although initially these are directed only against the preS2 epitope.

In terms of treating HBV chronic carriers, the murine model shown here demonstrates that T-cell non-responsiveness can be overcome by using DNA-mediated immunization. The induced response mimics in some aspects that required to clear a viral infection, namely an adequate cellular immune response to regulate viral gene expression without killing infected cells and an adequate humoral response to prevent the spread of free virus to uninfected cells. Thus, the inventors have arrived at the first demonstration of an immunotherapeutic application of DNA-mediated immunization against an infectious disease and particularly, provides a treatment for HBV chronic carriers.

TABLE I

Induction of antibodies against the hepatitis B surface antigen

| Description | Number of mice | Level of antibodies against hepatitis B surface antigen in the serum (mIU/ml) Before DNA injection | 15 days after DNA injection | 35 days after DNA injection |
| --- | --- | --- | --- | --- |
| DNA injected 1 day after marcaine treatment | 5 | 0 | average: 56 from 5 to >140 | average: 59 |
| DNA injected 5 days after marcaine treatment | 5 | 0 | average: 71 from 21 to >108 | average: 47 |

TABLE II

| Group | Luciferase RLU/sec/muscle (Average ± SEM) RLU = Relative Light Unit | Percentage relative to the control |
| --- | --- | --- |
| Control | 43 082 ± 5 419 | 100% |
| 4X DOGS | 28 ± 7 | 0.06% |
| DOGS - | 50 ± 23 | 0.12% |

TABLE II-continued

| Group | Luciferase RLU/sec/muscle (Average ± SEM) RLU = Relative Light Unit | Percentage relative to the control |
|---|---|---|
| Spermidine PEG-DOGS | 0 ± 0 | 0.00% |

TABLE III

Immunization with the Biojector$^R$

| pCMV-HB.S N° | 0 weeks | 2 weeks | 8 weeks |
|---|---|---|---|
| 2.1 | 0 | 517 | 380 |
| 2.2 | 0 | 374 | 322 |
| 3.1 | 0 | 258 | 418 |
| 4.1 | 0 | 400 | 4045 |
| 4.2 | 0 | 88 | 86 |
| 4.3 | 0 | 314 | 420 |
| 6.1 | 0 | 415 | 1001 |
| 6.2 | 0 | 1543 | 3517 |
| 6.3 | 0 | 1181 | 141 |
| Average | 0 | 566 mUI/ml | 1148 mUI/ml |

TABLE III-continued

Immunization with the Biojector$^R$

| pCMV-HB.S N° | 0 weeks | 2 weeks | 8 weeks |
|---|---|---|---|
| SD | 0 | 476 | 1521 |
| SEM | 0 | 159 | 507 |
| N | 9 | 9 | 9 |
| CV | | 84% | 133% |

TABLE IV

Immunization by injection using a needle

| pCMV-HB.S N° | 0 weeks | 2 weeks | 8 weeks |
|---|---|---|---|
| 1.1 | 1 | 2 | 1 |
| 5.1 | 0 | 287 | 186 |

TABLE IV-continued

Immunization by injection using a needle

| pCMV-HB.S N° | 0 weeks | 2 weeks | 8 weeks |
|---|---|---|---|
| 5.2 | 0 | 162 | 798 |
| 5.3 | 0 | 305 | 203 |
| 7.1 | 0 | 86 | 175 |
| 7.2 | 0 | 1108 | dead |
| Average | 0 | 325 mUI/ml | 273 mUI/ml |
| SD | 0 | 401 | 305 |
| SEM | 0 | 164 | 136 |
| N | 6 | 6 | 5 |
| CV | 245% | 124% | 112% |

TABLE V

Long term response of a mouse vaccinated with pCMVHB-S

| | 1 month | 2 months | 3 months | 6 months |
|---|---|---|---|---|
| a-HBs titre in mUI/ml | 227 | 662 | 1299 | 1082 |
| a-HBs ELISA titre | $3.5 \times 10^{-4}$ | $5 \times 10^{-4}$ | $8.5 \times 10^{-4}$ | $9 \times 10^{-4}$ |

TABLE VI

Serum titres of HBsAg in Tg mice passively transferred with antibodies to HBsAg.

| Mouse n° | Injected serum | Bleeding (days) | | | | | | | |
|---|---|---|---|---|---|---|---|---|---|
| | | 0 | 0.25 | 1 | 2 | 3 | 6 | 10 | 15 | 17 |
| 4-23 | NMS | 429 | 404 | 477 | 420 | 440 | 452 | ND | 252 | 502 † |
| 2-21 | anti-HBs Ab | 1321 | 0 | 13 | 61 | 373 | 725 | ND | 1028 | 1356 † |
| 6-11 | NMS | 696 | 548 | 442 † | | | | | | |
| 4-26 | anti-HBs Ab | 1080 | 0 | 22 † | | | | | | |
| 1-3-16 | NMS | 565 | ND | 542 | ND | 326 | 562 | 328 | 647 | 693 † |
| 1-3-5 | anti-HBs Ab | 721 | ND | 0 | ND | 0 | 0 | 0 | 3 | 0 † |
| 1-3-6 | anti-HBs Ab | 548 | ND | 3 | ND | 0 | 0 | 3 | 6 | 0 † |

Results are shown for seven Tg mice injected intraperitoneally once (mice 4-23, 2-21, 6-11 and 4-26) or every 2-3 days (mice 1-3-16, 1-3-5, 1-3-6) with either anti-HBs immune sera (anti-HBs Ab) or normal mouse sera (NMS). HBsAg titers (ng/ml) were determined in the sera collected at the indicated time. Mice were killed (†) 26 hours or 17 days after the transfer and their livers were harvested for extraction of mRNA and Northern blot analysis.
ND: Not Done

TABLE VII

Secretion of cytokines by spleen cells in culture.

| Mice | Cytokines | Medium | ConA | preS2 peptide | HBsAg |
|---|---|---|---|---|---|
| Non-Tg | IFN-γ | 2 ± 1 | 1,611 ± 377 | 92 ± 42 | 60 ± 28 |
| | TNF-α | 28 ± 13 | 846 ± 87 | 267 ± 23 | 58 ± 17 |
| | IL-2 | 2 ± 1 | 2,584 ± 233 | 3 ± 2 | 4 ± 2 |
| | IL-4 | 6 ± 4 | 62 ± 15 | 4 ± 4 | 8 ± 6 |
| Tg | IFN-γ | 2 ± 2 | 1,709 ± 12 | 329 ± 227 | 39 ± 25 |
| | TNF-α | 28 ± 12 | 871 ± 13 | 405 ± 137 | 83 ± 46 |
| | IL-2 | 1 ± 1 | 4,136 ± 578 | 1 ± 1 | 1 ± 1 |
| | IL-4 | 11 ± 8 | 49 ± 3 | 12 ± 6 | 11 ± 9 |

Splenocytes of pCMV-S2.S-immunized Tg and non-Tg mice were incubated with medium or stimulated with concanavalin A (ConA, 2.5 μg/ml), preS2 peptide (10 μg/ml) or HBsAg particles (3 μg/ml) for 72 hr. Antigen-specific culture supernatants were harvested for determination of cytokine levels (pg/ml) at 24 hr for TNF-α and IL-2 determinations and at 48 hr for IFN-γ and IL-4. Data are as the arithmetic mean ± SEM of 5 to 6 spleens independently tested in two experiments.

What is claimed is:

1. A method for breaking T-cell tolerance in a chronic HBV carrier comprising administering to the chronic HBV carrier a vector,
wherein the vector comprises a gene or a DNA encoding an antigenic portion of HBV S, preS$_2$-S, or preS$_1$-preS$_2$-S proteins of HBV operably linked to a promoter, and
wherein the vector is administered to the chronic HBV carrier in an amount sufficient to break T-cell tolerance.

2. The method of claim 1, wherein the vector is administered in an amount sufficient to induce a B cell response.

3. The method of claim 2, wherein the B cell response clears circulating HBsAg.

4. The method of claim 1, wherein the vector comprises a gene or a DNA encoding an antigenic portion of HBV S protein.

5. The method of claim 1, wherein the vector comprises a gene or a DNA encoding an antigenic portion of HBV preS$_2$-S protein.

6. The method of claim 1, wherein the vector comprises a gene or a DNA encoding an antigenic portion of HBV preS$_1$-preS$_2$-S protein.

7. The method of claim 1, wherein the promoter is a CMV promoter.

8. The method of claim 2, wherein the promoter is a CMV promoter.

9. The method of claim 3, wherein the promoter is a CMV promoter.

10. The method of claim 4, wherein the promoter is a CMV promoter.

11. The method of claim 5, wherein the promoter is a CMV promoter.

12. The method of claim 6, wherein the promoter is a CMV promoter.

13. The method of claim 1, wherein the promoter is an HBV promoter.

14. The method of claim 2, wherein the promoter is an HBV promoter.

15. The method of claim 3, wherein the promoter is an HBV promoter.

16. The method of claim 4, wherein the promoter is an HBV promoter.

17. The method of claim 5, wherein the promoter is an HBV promoter.

18. The method of claim 6, wherein the promoter is an HBV promoter.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
         (A) LENGTH: 5618 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 1:

```
GACGGATCGG GAGATCTCCC GATCCCCTAT GGTCGACTCT CAGTACAATC TGCTCTGATG     60
CCGCATAGTT AAGCCAGTAT CTGCTCCCTG CTTGTGTGTT GGAGGTCGCT GAGTAGTGCG    120
CGAGCAAAAT TTAAGCTACA ACAAGGCAAG GCTTGACCGA CAATTGCATG AAGAATCTGC    180
TTAGGGTTAG GCGTTTTGCG CTGCTTCGCG ATGTACGGGC CAGATATACG CGTTGACATT    240
GATTATTGAC TAGTTATTAA TAGTAATCAA TTACGGGGTC ATTAGTTCAT AGCCCATATA    300
TGGAGTTCCG CGTTACATAA CTTACGGTAA ATGGCCCGCC TGGCTGACCG CCCAACGACC    360
CCCGCCCATT GACGTCAATA ATGACGTATG TTCCCATAGT AACGCCAATA GGGACTTTCC    420
ATTGACGTCA ATGGGTGGAC TATTTACGGT AAACTGCCCA CTTGGCAGTA CATCAAGTGT    480
ATCATATGCC AAGTACGCCC CCTATTGACG TCAATGACGG TAAATGGCCC GCCTGGCATT    540
ATGCCCAGTA CATGACCTTA TGGGACTTTC CTACTTGGCA GTACATCTAC GTATTAGTCA    600
TCGCTATTAC CATGGTGATG CGGTTTTGGC AGTACATCAA TGGGCGTGGA TAGCGGTTTG    660
ACTCACGGGG ATTTCCAAGT CTCCACCCCA TTGACGTCAA TGGGAGTTTG TTTTGGCACC    720
AAAATCAACG GGACTTTCCA AAATGTCGTA ACAACTCCGC CCCATTGACG CAAATGGGCG    780
GTAGGCGTGT ACGGTGGGAG GTCTATATAA GCAGAGCTCT CTGGCTAACT AGAGAACCCA    840
CTGCTTAACT GGCTTATCGA AATTAATACG ACTCACTATA GGGAGACCCA AGCTTGGTAC    900
CGGGCCCCCC CTCGAGGATT GGGGACCCTG CGCTGAACAT GGAGAACATC ACATCAGGAT    960
TCCTAGGACC CCTTCTCGTG TTACAGGCGG GGTTTTTCTT GTTGACAAGA ATCCTCACAA   1020
TACCGCAGAG TCTAGACTCG TGGTGGACTT CTCTCAATTT TCTAGGGGGA ACTACCGTGT   1080
GTCTTGGCCA AAATTCGCAG TCCCCAACCT CCAATCACTC ACCAACCTCT TGTCCTCCAA   1140
CTTGTCCTGG TTATCGCTGG ATGTGTCTGC GGCGTTTTAT CATCTTCCTC TTCATCCTGC   1200
TGCTATGCCT CATCTTCTTG TTGGTTCTTC TGGACTATCA AGGTATGTTG CCCGTTTGTC   1260
CTCTAATTCC AGGATCCTCA ACAACCAGCA CGGGACCATG CCGGACCTGC ATGACTACTG   1320
CTCAAGGAAC CTCTATGTAT CCCTCCTGTT GCTGTACCAA ACCTTCGGAC GGAAATTGCA   1380
CCTGTATTCC CATCCCATCA TCCTGGGCTT TCGGAAAATT CCTATGGGAG TGGGCCTCAG   1440
CCCGTTTCTC CTGGCTCAGT TTACTAGTGC CATTTGTTCA GTGGTTCGTA GGGCTTTCCC   1500
CCACTGTTTG GCTTTCAGTT ATATGGATGA TGTGGTATTG GGGGCCAAGT CTGTACAGCA   1560
TCTTGAGTCC CTTTTTACCG CTGTTACCAA TTTTCTTTTG TCTTTGGGTA TACATTTAAA   1620
CCCTAACAAA ACAAGAGAT GGGGTTACTC TCTAAATTTT ATGGGTTATG TCATTGGATG   1680
TTATGGGTCC TTGCCACAAG AACACATCAT ACAAAAAATC AAGAATGTT TTAGAAAACT   1740
TCCTATTAAC AGGCCTATTG ATTGGAAAGT ATGTCAACGA ATTGTGGGTC TTTTGGGTTT   1800
```

```
TGCTGCCCCT TTTACACAAT GTGGTTATCC TGCGTTGATG CCTTTGTATG CATGTATTCA    1860

ATCTAAGCAG GCTTTCACTT TCTCGCCAAC TTACAAGGCC TTTCTGTGTA AACAATACCT    1920

GAACCTTTAC CCCGTTGCCC GGCAACGGCC AGGTCTGTGC CAAGTGTTTG CTGACGCAAC    1980

CCCCACTGGC TGGGGCTTGG TCATGGGCCA TCAGCGCATG CGTGGAACCT TTTCGGCTCC    2040

TCTGCCGATC CATACTGCGG AACTCCTAGC CGCTTGTTTT GCTCGCAGCA GGTCTGGAGC    2100

AAACATTATC GGGACTGATA ACTCTGTTGT CCTATCCCGC AAATATACAT CGTTTCCATG    2160

GCTGCTAGGC TGTGCTGCCA ACTGGATCCT GCGCGGGACG TCCTTTGTTT ACGTCCCGTC    2220

GGCGCTGAAT CCTGCGGACG ACCCTTCTCG GGTCGCTTG GGACTCTCTC GTCCCCTTCT    2280

CCGTCTGCCG TTCCGACCGA CCACGGGGCG CACCTCTCTT TACGCGGACT CCCCGTCTGT    2340

GCCTTCTCAT CTGCCGGACC GTGTGCACTT CGCTTCACCT CTGCACGTCG CATGGAGACC    2400

ACCGTGAACG CCCACCAAAT ATTGCCCAAG GTCTTACATA AGAGGACTCT TGGACTCTCA    2460

GCAATGTCAA CGACCGACCT TGAGGCATAC TTCAAAGACT GTTTGTTTAA AGACTGGGAG    2520

GAGTTGGGGG AGGAGATTAG GTTAAAGGTC TTTGTACTAG GAGGCTGTAG GCATAAATTG    2580

GTCTGCGCAC CAGCACCATG CAACTTTTTC ACCTCTGCCT AATCATCTCT TGTTCATGTC    2640

CTACTGTTCA AGCCTCCAAG CTGTGCCTTG GGTGGCTTTG GGGCATGGAC ATCGACCCTT    2700

ATAAAGAATT TGGAGCTACT GTGGAGTTAC TCTCGTTTTT GCCTTCTGAC TTCTTTCCTT    2760

CAGTACGAGA TCTGGCCAGG ATCCACTAGT TCTAGAGCGG CCGCCACCGC GGTGGAGCTC    2820

CAGCTTTTGT TCCCTTTAGT GAGGGTTAAT TGCGCGCATG CCCGACGGCG AGGATCTCGT    2880

CGTGACCCAT GGCGATGCCT GCTTGCCGAA TATCATGGTG GAAAATGGCC GCTTTTCTGG    2940

ATTCATCGAC TGTGGCCGGC TGGGTGTGGC GGACCGCTAT CAGGACATAG CGTTGGCTAC    3000

CCGTGATATT GCTGAAGAGC TTGGCGGCGA ATGGGCTGAC CGCTTCCTCG TGCTTTACGG    3060

TATCGCCGCT CCCGATTCGC AGCGCATCGC CTTCTATCGC CTTCTTGACG AGTTCTTCTG    3120

AGCGGGACTC TGGGGTTCGA AATGACCGAC CAAGCGACGC CCAACCTGCC ATCACGAGAT    3180

TTCGATTCCA CCGCCGCCTT CTATGAAAGG TTGGGCTTCG GAATCGTTTT CCGGACGCC    3240

GGCTGGATGA TCCTCCAGCG CGGGGATCTC ATGCTGGAGT TCTTCGCCCA CCCCAACTTG    3300

TTTATTGCAG CTTATAATGG TTACAAATAA AGCAATAGCA TCACAAATTT CACAAATAAA    3360

GCATTTTTTT CACTGCATTC TAGTTGTGGT TTGTCCAAAC TCATCAATGT ATCTTATCAT    3420

GTCTGGATCC CGTCGACCTC GAGAGCTTGG CGTAATCATG GTCATAGCTG TTTCCTGTGT    3480

GAAATTGTTA TCCGCTCACA ATTCCACACA ACATACGAGC CGGAAGCATA AAGTGTAAAG    3540

CCTGGGGTGC CTAATGAGTG AGCTAACTCA CATTAATTGC GTTGCGCTCA CTGCCCGCTT    3600

TCCAGTCGGG AAACCTGTCG TGCCAGCTGC ATTAATGAAT CGGCCAACGC GCGGGGAGAG    3660

GCGGTTTGCG TATTGGGCGC TCTTCCGCTT CCTCGCTCAC TGACTCGCTG CGCTCGGTCG    3720

TTCGGCTGCG GCGAGCGGTA TCAGCTCACT CAAAGGCGGT AATACGGTTA TCCACAGAAT    3780

CAGGGGATAA CGCAGGAAAG AACATGTGAG CAAAAGGCCA GCAAAAGGCC AGGAACCGTA    3840

AAAAGGCCGC GTTGCTGGCG TTTTTCCATA GGCTCCGCCC CCTGACGAG CATCACAAAA    3900

ATCGACGCTC AAGTCAGAGG TGGCGAAACC CGACAGGACT ATAAAGATAC CAGGCGTTTC    3960

CCCCTGGAAG CTCCCTCGTG CGCTCTCCTG TTCCGACCCT GCCGCTTACC GGATACCTGT    4020

CCGCCTTTCT CCCTTCGGGA AGCGTGGCGC TTTCTCAATG CTCACGCTGT AGGTATCTCA    4080

GTTCGGTGTA GGTCGTTCGC TCCAAGCTGG GCTGTGTGCA CGAACCCCCC GTTCAGCCCG    4140
```

```
ACCGCTGCGC CTTATCCGGT AACTATCGTC TTGAGTCCAA CCCGGTAAGA CACGACTTAT   4200

CGCCACTGGC AGCAGCCACT GGTAACAGGA TTAGCAGAGC GAGGTATGTA GGCGGTGCTA   4260

CAGAGTTCTT GAAGTGGTGG CCTAACTACG GCTACACTAG AAGGACAGTA TTTGGTATCT   4320

GCGCTCTGCT GAAGCCAGTT ACCTTCGGAA AAAGAGTTGG TAGCTCTTGA TCCGGCAAAC   4380

AAACCACCGC TGGTAGCGGT GGTTTTTTTG TTTGCAAGCA GCAGATTACG CGCAGAAAAA   4440

AAGGATCTCA AGAAGATCCT TTGATCTTTT CTACGGGGTC TGACGCTCAG TGGAACGAAA   4500

ACTCACGTTA AGGGATTTTG GTCATGAGAT TATCAAAAAG GATCTTCACC TAGATCCTTT   4560

TAAATTAAAA ATGAAGTTTT AAATCAATCT AAAGTATATA TGAGTAAACT TGGTCTGACA   4620

GTTACCAATG CTTAATCAGT GAGGCACCTA TCTCAGCGAT CTGTCTATTT CGTTCATCCA   4680

TAGTTGCCTG ACTCCCCGTC GTGTAGATAA CTACGATACG GGAGGGCTTA CCATCTGGCC   4740

CCAGTGCTGC AATGATACCG CGAGACCCAC GCTCACCGGC TCCAGATTTA TCAGCAATAA   4800

ACCAGCCAGC CGGAAGGGCC GAGCGCAGAA GTGGTCCTGC AACTTTATCC GCCTCCATCC   4860

AGTCTATTAA TTGTTGCCGG GAAGCTAGAG TAAGTAGTTC GCCAGTTAAT AGTTTGCGCA   4920

ACGTTGTTGC CATTGCTACA GGCATCGTGG TGTCACGCTC GTCGTTTGGT ATGGCTTCAT   4980

TCAGCTCCGG TTCCCAACGA TCAAGGCGAG TTACATGATC CCCCATGTTG TGCAAAAAAG   5040

CGGTTAGCTC CTTCGGTCCT CCGATCGTTG TCAGAAGTAA GTTGGCCGCA GTGTTATCAC   5100

TCATGGTTAT GGCAGCACTG CATAATTCTC TTACTGTCAT GCCATCCGTA AGATGCTTTT   5160

CTGTGACTGG TGAGTACTCA ACCAAGTCAT TCTGAGAATA GTGTATGCGG CGACCGAGTT   5220

GCTCTTGCCC GGCGTCAATA CGGGATAATA CCGCGCCACA TAGCAGAACT TTAAAAGTGC   5280

TCATCATTGG AAAACGTTCT TCGGGGCGAA AACTCTCAAG GATCTTACCG CTGTTGAGAT   5340

CCAGTTCGAT GTAACCCACT CGTGCACCCA ACTGATCTTC AGCATCTTTT ACTTTCACCA   5400

GCGTTTCTGG GTGAGCAAAA ACAGGAAGGC AAAATGCCGC AAAAAAGGGA ATAAGGGCGA   5460

CACGGAAATG TTGAATACTA ATACTCTTCC TTTTTCAATA TTATTGAAGC ATTTATCAGG   5520

GTTATTGTCT CATGAGCGGA TACATATTTG AATGTATTTA GAAAAATAAA CAAATAGGGG   5580

TTCCGCGCAC ATTTCCCCGA AAAGTGCCAC CTGACGTC                          5618
```